United States Patent [19]

Jeganathan

[11] Patent Number: 5,763,144
[45] Date of Patent: Jun. 9, 1998

[54] COLOR-PHOTOGRAPHIC RECORDING MATERIAL

[75] Inventor: Suruliappa Jeganathan, Fribourg, Switzerland

[73] Assignee: Ciba Specialty Chemicals Corporation, Tarrytown, N.Y.

[21] Appl. No.: 693,186
[22] PCT Filed: Feb. 1, 1995
[86] PCT No.: PCT/EP95/00347
 § 371 Date: Aug. 5, 1996
 § 102(e) Date: Aug. 5, 1996
[87] PCT Pub. No.: WO95/22082
 PCT Pub. Date: Aug. 17, 1995

[30] Foreign Application Priority Data

Feb. 11, 1994 [CH] Switzerland ............... 414/94

[51] Int. Cl.$^6$ ................................ G03C 11/00
[52] U.S. Cl. .............. 430/372; 430/551; 430/554; 430/555; 430/558; 544/63; 544/93; 544/106; 544/336; 549/13; 549/14
[58] Field of Search .................. 430/372, 551, 430/554, 555, 558; 544/63, 98, 106, 336; 549/13, 14

[56] References Cited

U.S. PATENT DOCUMENTS

| | | | |
|---|---|---|---|
| 5,362,615 | 11/1994 | Hagemann et al. | 430/551 |
| 5,484,696 | 1/1996 | Jain et al. | 430/551 |
| 5,561,037 | 10/1996 | Jain et al. | 430/551 |

FOREIGN PATENT DOCUMENTS

| | | |
|---|---|---|
| 0273712 | 7/1988 | European Pat. Off. . |
| 63-311353 | 12/1988 | Japan . |

OTHER PUBLICATIONS

B.K. Wasson et al., Journal of Medicinal Chemistry, vol. 15, No. 6, pp. 651–655, (1972).

Primary Examiner—Geraldine Letscher
Attorney, Agent, or Firm—Luther A. R. Hall; Michele Kovaleski

[57] ABSTRACT

The invention relates to a color-photographic recording material which comprises a magenta coupler and, as stabilizer, at least one compound of formula (Ia), (Ib) or (II), where the radicals are as defined in claim 1, and to the novel stabilizers.

9 Claims, No Drawings

COLOR-PHOTOGRAPHIC RECORDING MATERIAL

The present invention relates to a novel colour-photographic recording material which contains a magenta coupler and, as stabilizer, an N-heterocyclylphenyl compound, and to novel N-heterocyclylphenyl compounds.

The alkylated hydroquinone ethers or diethers used hitherto as stabilizers in photographic materials exhibited inadequate activity, in particular in the case of 1H-pyrazolo-[5,1-c][1,2,4]triazole magenta couplers (see also structure C-5).

A group of N-heterocyclylphenyl compounds has now been found which, surprisingly, has proved substantially free from such disadvantages. In addition, they are also suitable as coupler oils and thus facilitate a simplified incorporation of the couplers. In particular, this group of N-heterocyclylphenyl compounds is suitable for increasing the stability of magenta dyes in colour-photographic materials.

The novel stabilizers can be used for all types of photosensitive materials. For example, they can be employed for colour paper, colour reversal paper, direct-positive colour material, colour negative film, colour positive film, colour reversal film, etc. They are preferably used, inter alia, for photosensitive colour material which contains a reversal substrate or forms positives.

Colour-photographic recording materials usually contain, on a support, a blue-sensitive and/or a green-sensitive and/or a red-sensitive silver-halide emulsion layer and, if desired, a protection layer, the stabilizer for the magenta dye being in the green-sensitive layer.

The present application thus relates to a colour-photographic recording material which contains a magenta coupler and, as stabilizer, at least one compound of the formula

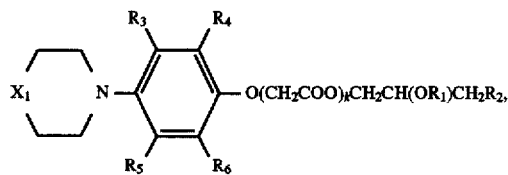

(Ia)

or

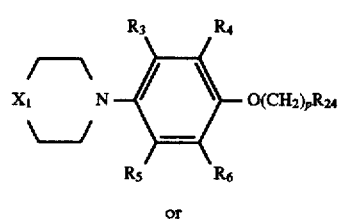

(Ib)

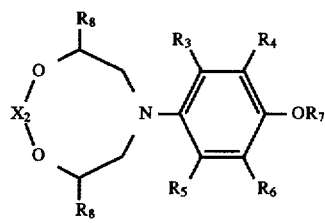

(II)

where
k is the number 0 or 1;
p is a number from 1 to 18;
$R_1$ is hydrogen, $C_1$–$C_{12}$alkyl, $C_1$–$C_{12}$alkoxy, —$COR_9$, —$COOR_{10}$ or —$Si(R_{11})(R_{12})(R_{13})$;
in which $R_9$ is $C_1$–$C_8$alkyl, $C_2$–$C_{18}$alkenyl or phenyl;
$R_{10}$ is $C_1$–$C_4$alkyl or benzyl; and
$R_{11}$, $R_{12}$ and $R_{13}$, independently of one another, are $C_1$–$C_6$alkyl or phenyl;
$R_2$ is hydrogen, $C_1$–$C_{18}$alkyl, —$OR_{14}$ or —$(CH_2)_n COOR_{15}$;
in which n is a number from 0 to 17;
$R_{14}$ is hydrogen, $C_1$–$C_{18}$alkyl, $C_2$–$C_{18}$alkenyl, phenyl-$C_1$–$C_4$alkyl, $C_3$–$C_{24}$alkyl which is interrupted by one or more —O— atoms, $C_2$–$C_{14}$hydroxyalkyl, phenyl, which may be monosubstituted to trisubstituted by $C_1$–$C_4$alkyl, $C_1$–$C_4$alkoxy or halogen, or is tolyl, $C_5$–$C_6$cycloalkyl or —$COR_{16}$;
$R_{15}$ is $C_1$–$C_{18}$alkyl, $C_2$–$C_{18}$alkenyl or phenyl, which may be monosubstituted to trisubstituted by $C_1$–$C_4$alkyl, $C_1$–$C_4$alkoxy or halogen;
in which $R_{16}$ is $C_1$–$C_{18}$alkyl, $C_2$–$C_{18}$alkenyl or phenyl;
$R_3$, $R_4$, $R_5$ and $R_6$, independently of one another, are hydrogen, $C_1$–$C_{12}$alkyl, $C_1$–$C_8$alkoxy, $C_5$–$C_7$cycloalkyl, phenyl, phenyl-$C_1$–$C_4$alkyl or halogen; $R_7$ is hydrogen, $C_1$–$C_{18}$alkyl, $C_2$–$C_{18}$alkenyl, phenyl-$C_1$–$C_4$alkyl, $C_3$–$C_{24}$alkyl, which is interrupted by one or more —O— atoms, phenyl-$C_1$–$C_4$alkyl, phenyl, which may be monosubstituted to trisubstituted by $C_1$–$C_4$alkyl, $C_1$–$C_4$alkoxy or halogen, or is benzyl, a group of the formula

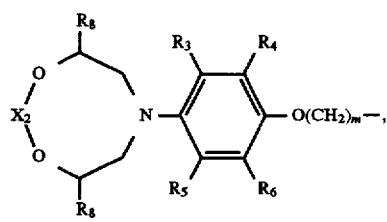

—$CH_2COOR_{23}$ or —$(CH_2COO)_k CH_2CH(OR_1)CH_2R_{17}$;
in which k is the number 0 or 1;
m is a number from 1 to 17;
$R_{17}$ is as defined for $R_2$ or is a group of the formula

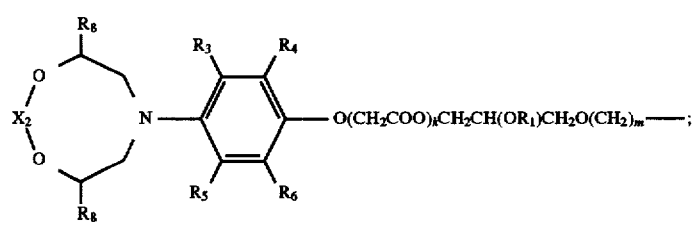

and $R_{23}$ is $C_1-C_8$alkyl;

$R_8$ is hydrogen, $C_1-C_{18}$alkyl or $CH_2R_2$; $R_{24}$ is $-Si(R_{11})(R_{12})(R_{13})$ or a group of the formula

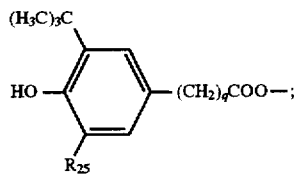

in which q is a number from 0 to 12; and $R_{25}$ is hydrogen or $C_1-C_{18}$alkyl;

$X_1$ is O, S, SO, $SO_2$ or $NR_{18}$;

in which $R_{18}$ is hydrogen, $C_1-C_{18}$alkyl, $-CH_2CH(OH)CH_2O(C_1-C_{14}$alkyl) or $-CO-R_{19}$;

in which $R_{19}$ is $C_1-C_{18}$alkyl; and $X_2$ is CO, $BR_{20}$, $PR_{21}$, $P(O)R_{22}$, SO or $SO_2$;

in which $R_{20}$, $R_{21}$, and $R_{22}$ are $C_1-C_{18}$alkyl or phenyl, which may be monosubstituted to trisubstituted by $C_1-C_4$alkyl, $C_1-C_4$alkoxy or halogen; and $R_{21}$ and $R_{22}$ may alternatively be phenoxy, which may be monosubstituted to trisubstituted by $C_1-C_4$alkyl, $C_1-C_4$alkoxy or halogen;

where, in the case of compounds of the formula (Ia) $R_2$ may alternatively be a group of the formula

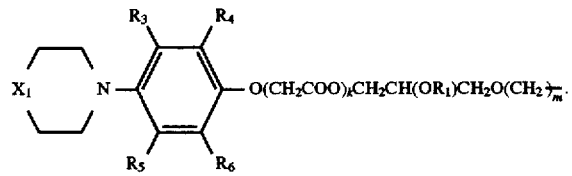

Any $C_1-C_{18}$alkyl substituents in the compounds according to the invention are radicals such as methyl, ethyl, propyl, butyl, pentyl, hexyl, heptyl, octyl, nonyl, decyl, undecyl, dodecyl, tetradecyl, hexadecyl and octadecyl, and corresponding branched isomers.

$C_5-C_7$cycloalkyl radicals are, for example, cyclopentyl, cyclohexyl or cycloheptyl.

Alkyl radicals having 3 to 24 carbon atoms which are interrupted by oxygen are, for example,

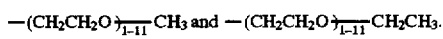

Alkenyl radicals having 2 to 18 carbon atoms may be monounsaturated or, from 4 carbon atoms, polyunsaturated, for example, 1-propenyl, allyl, methallyl, 2-butenyl, 2-pentenyl, 2-hexenyl, 2-octenyl, 4-tert-butyl-2-butenyl or radicals derived from the above alkyl radicals.

$C_1-C_{12}$alkoxy radicals are, for example, methoxy, ethoxy, propoxy, butoxy or hexoxy and corresponding branched isomers.

Phenyl-$C_1-C_4$alkyl radicals are, for example, benzyl or cumyl.

$C_2-C_{14}$hydroxyalkyl radicals are, for example, 2-hydroxyethyl, 2-hydroxypropyl, 3-hydroxypropyl, 2-hydroxybutyl or 4-hydroxybutyl.

Halogen radicals are, for example, fluorine, chlorine, bromine or iodine. Preferably, halogen is chlorine.

Preferably, $R_1$ is hydrogen.

Preferably, $R_2$ is $C_1-C_{18}$alkyl or $-OR_{14}$;

in which $R_{14}$ is hydrogen, $C_1-C_{18}$alkyl, $C_2-C_{18}$alkenyl, $C_3-C_{24}$alkych is interrupted by one or more —O— atoms, phenyl, which may be monosubstituted to trisubstituted by $C_1-C_4$alkyl or $C_1-C_4$alkoxy, or is tolyl or $C_5-C_6$cycloalkyl;

and, in the case of compounds of the formula (Ia), may alternatively be a group of the formula

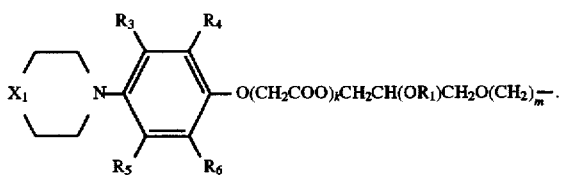

Preferably, $R_3$, $R_4$, $R_5$ and $R_6$, independently of one another, are hydrogen, $C_1-C_{12}$alkyl or $C_1-C_8$alkoxy; and most preferably $R_3$, $R_4$, $R_5$ and $R_6$ are hydrogen.

Preferably, $R_7$ is $C_1-C_{18}$alkyl, $C_2-C_{18}$alkenyl, a group of the formula

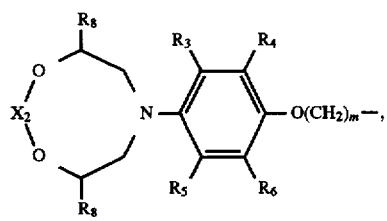

$-CH_2COOR_{23}$ or $-(CH_2COO)_kCH_2CH(OR_1)CH_2R_{17}$;

in which k is the number 0 or 1;

m is a number from 1 to 17;

$R_{17}$ is as defined for $R_2$ or is a group of the formula

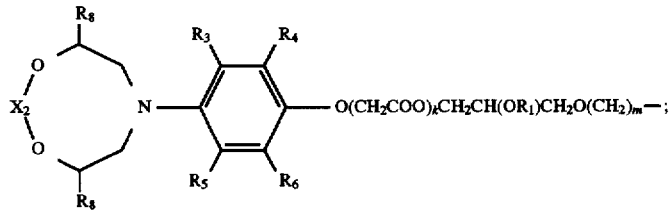

and $R_{23}$ is $C_1$–$C_8$alkyl.

Preferably, $R_8$ is hydrogen, $C_1$–$C_8$alkyl or $CH_2R_2$.

Preferably, $R_{24}$ is —Si($R_{11}$)($R_{12}$)($R_{13}$) or a group of the formula

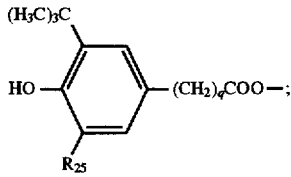

in which q is a number from 0 to 6;

$R_{11}$, $R_{12}$ and $R_{13}$, independently of one another, are $C_1$–$C_6$alkyl or phenyl; and $R_{25}$ is hydrogen or $C_1$–$C_{18}$alkyl.

Preferably, $X_1$ is O, S, SO, $SO_2$ or $NR_{18}$;

in which $R_{18}$ is —$CH_2CH(OH)CH_2O(C_1$–$C_{14}$alkyl);

and most preferably $X_1$ is O or $SO_2$.

Preferably, $X_2$ is CO, $BR_{20}$, $PR_{21}$ or $P(O)R_{22}$;

in which $R_{20}$, $R_{21}$ and $R_{22}$ are phenyl, which may be monosubstituted to trisubstituted by $C_1$–$C_4$alkyl, or $C_1$–$C_4$alkoxy; and $R_{21}$ and $R_{22}$ may alternatively be phenoxy, which may be monosubstituted to trisubstituted by $C_1$–$C_4$alkyl or $C_1$–$C_4$alkoxy;

and most preferably $X_2$ is $P(O)R_{22}$ in which $R_{22}$ is phenyl or phenoxy.

Preference is given to compounds of the formulae (Ia), (Ib) or (II).

where k is the number 0 or 1;

p is a number from 2 to 12;

$R_1$ is hydrogen;

$R_2$ is $C_1$–$C_{18}$alkyl or —$OR_{14}$;

in which $R_{14}$ is hydrogen, $C_1$–$C_{18}$alkyl, $C_2$–$C_{18}$alkenyl, $C_3$–$C_{24}$alkyl which is interrupted by one or more —O— atoms, phenyl, which may be monosubstituted to trisubstituted by $C_1$–$C_4$alkyl or $C_1$–$C_4$alkoxy, or is tolyl or $C_5$–$C_6$cycloalkyl;

$R_3$, $R_4$, $R_5$ and $R_6$, independently of one another, are hydrogen, $C_1$–$C_{12}$alkyl or $C_1$–$C_8$alkoxy;

$R_7$ is $C_1$–$C_{18}$alkyl, $C_2$–$C_{18}$alkenyl, a group of the formula

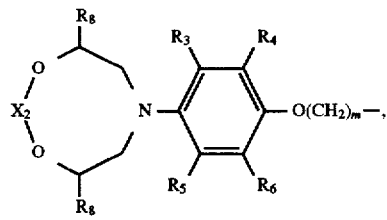

—$CH_2COOR_{23}$ or —$(CH_2COO)_kCH_2CH(OR_1)CH_2R_{17}$;

in which k is the number 0 or 1;

m is a number from 1 to 17;

$R_{17}$ is as defined for $R_2$ or is a group of the formula

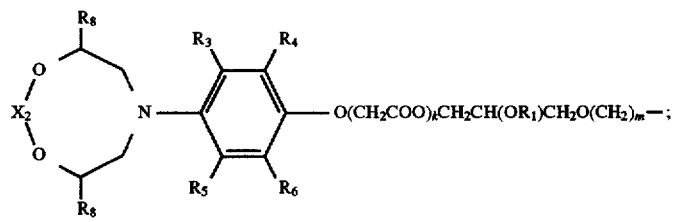

and $R_{23}$ is $C_1$–$C_8$alkyl;

$R_8$ is hydrogen, $C_1$–$C_8$alkyl or $CH_2R_2$;

$R_{24}$ is —Si($R_{11}$)($R_{12}$)($R_{13}$) or a group of the formula

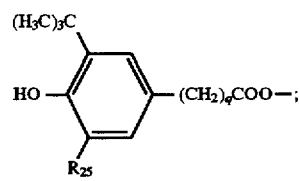

in which q is a number from 0 to 6;

$R_{11}$, $R_{12}$ and $R_{13}$, independently of one another, are $C_1$–$C_6$alkyl or phenyl; and $R_{25}$ is hydrogen or $C_1$–$C_{18}$alkyl;

$X_1$ is O, S, SO, $SO_2$ or $NR_{18}$;

in which $R_{18}$ is —$CH_2CH(OH)CH_2O(C_1$–$C_{14}$alkyl); and $X_2$ is CO, $BR_{20}$, $PR_{21}$ or $P(O)R_{22}$;

in which $R_{20}$, $R_{21}$ and $R_{22}$ are phenyl, which may be monosubstituted to trisubstituted by $C_1$–$C_4$alkyl or $C_1$–$C_4$alkoxy; and $R_{21}$ and $R_{22}$ may alternatively be phenoxy, which may be monosubstituted to trisubstituted by $C_1$–$C_4$alkyl or $C_1$–$C_4$alkoxy;

where, in the case of compounds of the formula (Ia), $R_2$ may alternatively be a group of the formula

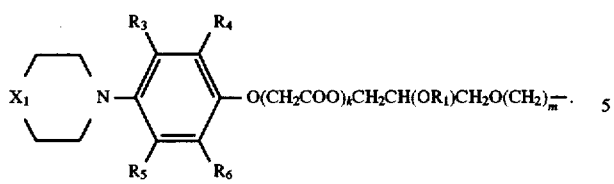

Particular preference is given to compounds of the formulae (Ia), (Ib) and (II) which have a melting point of below 60° C. or are liquid at room temperature. These compounds can be employed as photographic oil or partly replace the photographic oil.

Of particular importance are compounds of the formula (Ia), (Ib) or (II), where k is the number 0;

p is a number from 2 to 12;

$R_1$ is hydrogen;

$R_2$ is —$OR_{14}$;

in which $R_{14}$ is $C_1$–$C_{18}$alkyl, $C_3$–$C_{24}$alkyl which is interrupted by one or more —O— atoms, or phenyl;

$R_3$, $R_4$, $R_5$ and $R_6$ are hydrogen;

$R_7$ is $C_1$–$C_{18}$alkyl or —$(CH_2COO)_k CH_2CH(OR_1)CH_2R_{17}$;

in which k is the number 0; and $R_{17}$ is as defined for $R_2$;

$R_8$ is hydrogen or $CH_2R_2$;

$R_{24}$ is a group of the formula

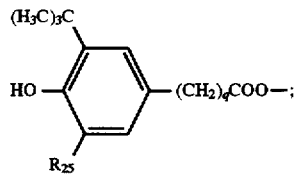

in which q is a number from 0 to 6; and $R_{25}$ is hydrogen or $C_1$–$C_{18}$alkyl;

$X_1$ is O or $SO_2$; and $X_2$ is $P(O)R_{22}$;

in which $R_{22}$ is phenyl or phenoxy.

Very particular preference is given to compounds of the formula (Ia) or (II), where k is the number 0;

$R_1$ is hydrogen;

$R_2$ is —$OR_{14}$;

in which $R_{14}$ is $C_1$–$C_{14}$alkyl or phenyl;

$R_3$, $R_4$, $R_5$ and $R_6$ are hydrogen;

$R_7$ is $C_1$–$C_{18}$alkyl;

$R_8$ is hydrogen or $CH_2R_2$;

$X_1$ is O or $SO_2$; and $X_2$ is $P(O)R_{22}$;

in which $R_{22}$ is phenyl or phenoxy.

The novel material preferably contains gelatin interlayers between the silver-halide emulsion layers.

Preference is given to photographic materials of this type in which the silver-halide in the blue-sensitive and/or green-sensitive and/or red-sensitive layer is silver chloride bromide comprising at least 90 mol % of silver chloride.

Preference is furthermore given to photographic materials which contain the silver-halide emulsion layers in the sequence blue-sensitive, green-sensitive and red-sensitive layers.

Typical and preferred stabilizers according to the invention are the following:

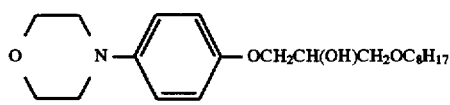 (100)

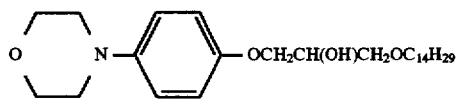 (101)

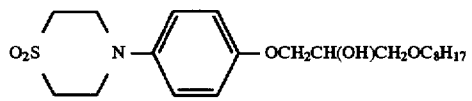 (102)

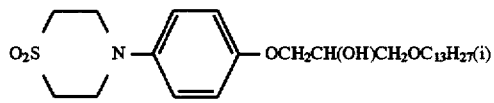 (103)

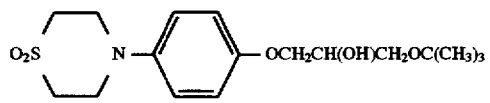 (104)

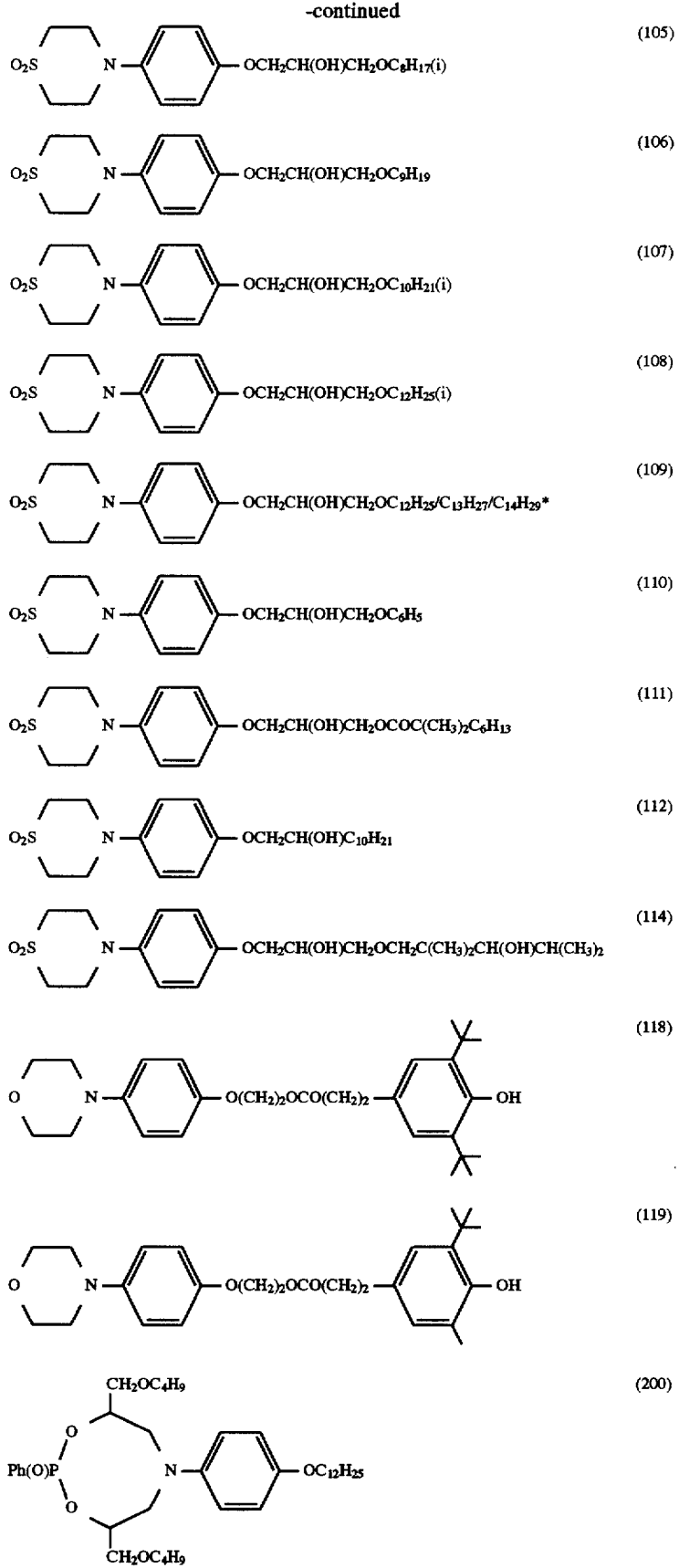

-continued

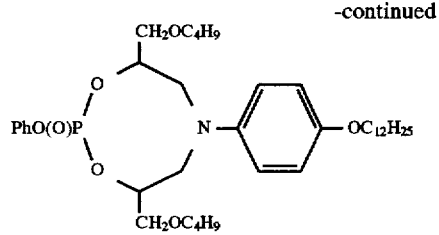
(201)

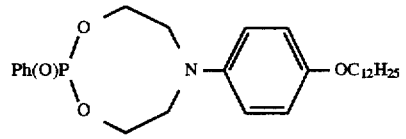
(202)

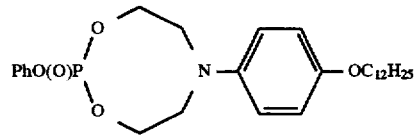
(203)

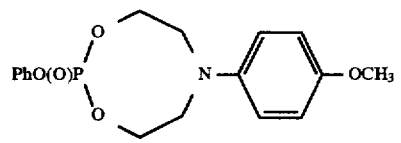
(204)

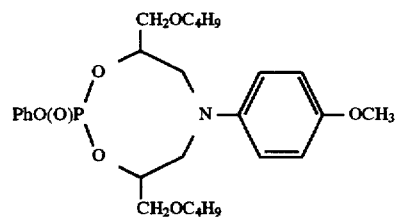
(205)

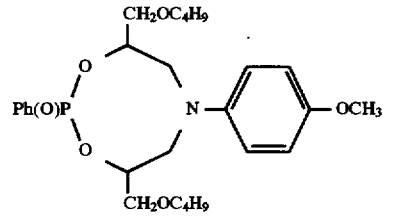
(206)

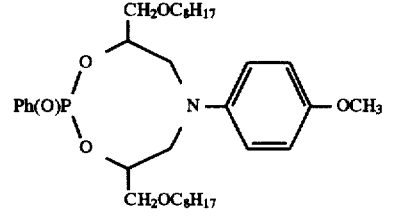
(207)

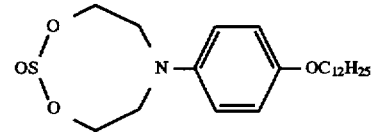
(208)

In the above compounds, "Ph" is a phenyl radical and "$C_{12}H_{25}/C_{13}H_{27}/C_{14}H_{29}$*" stands for a mixture of dodecyl, tridecyl and tetradecyl radicals.

In general, the novel stabilizers are used in from 0.1 to 4 times, preferably from 0.2 to 2 times, the amount by weight relative to the colour coupler used together with them.

The magenta couplers in the colour-photographic recording material can be, for example, simple 1-aryl-5-pyrazolones or pyrazole derivatives which are fused to 5-membered heterocyclic rings, eg. imidazopyrazoles, pyrazolopyrazoles, pyrazolotriazoles or pyrazolotetrazoles.

A group of magenta couplers comprises 5-pyrazolones of the formula C

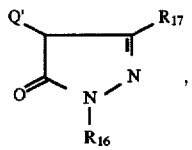

as described in British Patent 2 003 473. In this formula, $R_{16}$ is hydrogen, alkyl, aryl, alkenyl or a heterocyclic group. $R_{17}$ is hydrogen, alkyl, aryl, a heterocyclic group, an ester group, an alkoxy group, an alkylthio group, a carboxyl group, an arylamino group, an acylamino group, a (thio)urea group, a (thio)carbamoyl group, a guanidino group or a sulfonamido group.

$R_{17}$ is preferably a

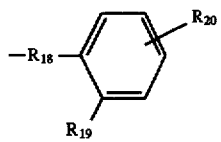

group, in which $R_{18}$ is imino, acylamino or ureido, $R_{19}$ is hydrogen, halogen, alkyl or alkoxy, $R_{20}$ is hydrogen, alkyl, acylamino, carbamoyl, sulfamoyl, sulfonamido, alkoxycarbonyl, acyloxy or a urethane group.

If Q' is hydrogen, the magenta coupler is tetraequivalent with respect to the silver halide.

Preferred examples of magenta couplers of this type are compounds of the formula

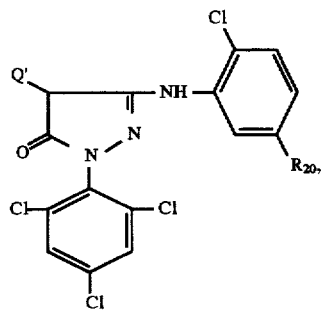

in which $R_{20}$ is as defined above, and Q', as described above, is a leaving group. These compounds are preferably present in the material according to the invention.

Further examples of tetraequivalent magenta couplers of this type are given in U.S. Pat. Nos. 2,983,608, 3,061,432, 3,062,653, 3,127,269, 3,152,896, 3,311,476, 3,419,391, 3,519,429, 3,558,319, 3,582,322, 3,615,506, 3,684,514, 3,834,908, 3,888,680, 3,891,445, 3,907,571, 3,928,044, 3,930,861, 3,930,866 and 3,933,500 and JP-A 89/309 058.

If Q' in the formula C is not hydrogen, but instead a group which is eliminated during the reaction with the oxidized developer, the magenta coupler is diequivalent. In this case, Q can be, for example, halogen or a group bonded to the pyrazole ring via O, S or N. Diequivalent couplers of this type give greater colour density and are more reactive towards the oxidized developer than are the corresponding tetraequivalent magenta couplers.

Examples of diequivalent magenta couplers are described in U.S. Pat. Nos. 3,006,579, 3,419,391, 3,311,476, 3,432, 521, 3,214,437, 4,032,346, 3,701,783, 4,351,897, 3,227,554, in EP-A 133 503, DE-A 2 944 601, JP-A 78/34 044, 74/53 435, 74/53 436, 75/53 372 and 75/122 935.

Typical and preferred magenta couplers conform to the formulae:

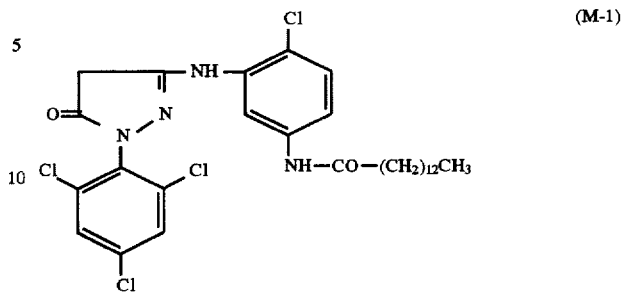

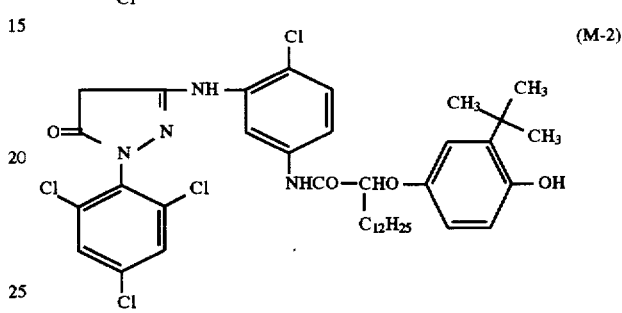

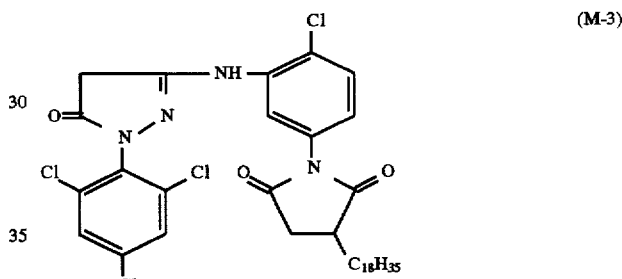

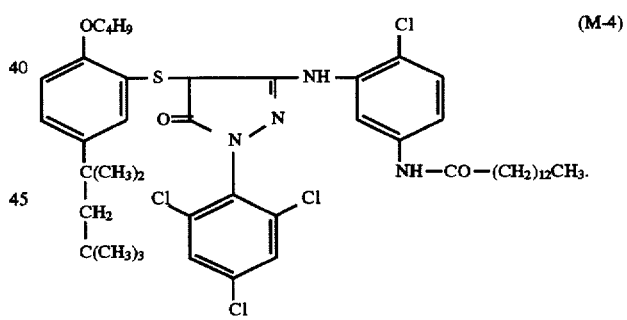

It is possible for 2 pyrazolone rings to be linked via a divalent Q', giving so-called bis-couplers. These are described, for example, in U.S. Pat. No. 2,632,702, U.S. Pat. No. 2,618,864, GB-A 968 461, GB-A 786 859, JP-A 76/37 646, 59/4086, 69/16 110, 69/26 589, 74/37 854 and 74/29 638. Y is preferably an O-alkoxyarylthio group.

As mentioned above, the magenta couplers used can also be pyrazoles fused to 5-membered heterocyclic rings, known as pyrazoloazoles. Their advantages over simple pyrazoles are that they give dyes of greater formalin resistance and have purer absorption spectra.

Magenta couplers of the pyrazoloazole type, which are likewise preferred, may be represented by the formula

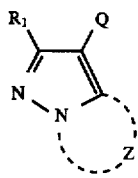
(C-2)

in which $R_1$ is hydrogen or a substituent, Z represents the non-metallic atoms necessary to complete a 5-membered ring containing 2 or 3 nitrogen atoms, it being possible for this ring to be substituted, and Q is hydrogen or a leaving group.

Of these compounds, preference is given to magenta couplers of the formulae

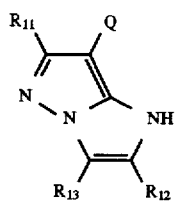
(C-3)

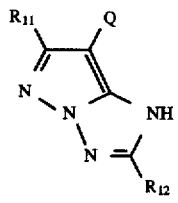
(C-4)

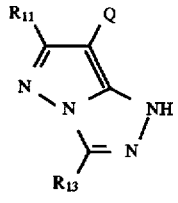
(C-5)

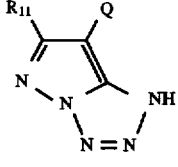
(C-6)

$R_{11}$, $R_{12}$ and $R_{13}$, independently of one another, are, for example, hydrogen, halogen, —$CR_3$ in which the radicals R, independently of one another, are hydrogen or alkyl, aryl, heterocyclyl, cyano, hydroxyl, nitro, carboxyl, amino, alkoxy, aryloxy, acylamino, alkylamino, anilino, ureido, sulfamoylamino, alkylthio, arylthio, alkoxycarbonylamino, sulfonamido, carbamoyl, sulfamoyl, sulfonyl, alkoxycarbonyl, heterocyclyloxy, azo, acyloxy, carbamoyloxy, silyloxy, aryloxycarbonylamino, imido, heterocyclylthio, sulfinyl, phosphonyl, aryloxycarbonyl, acyl or azolyl, preferably hydrogen, halogen (for example chlorine or bromine), —$CR_3$ in which the radicals $R_3$, independently of one another, are hydrogen or alkyl, aralkyl, alkenyl, alkynyl, cycloalkyl or cycloalkenyl, particularly preferably methyl, ethyl, propyl, isopropyl, t-butyl, tridecyl, 2-methanesulfonylethyl, 3-(3-pentadecylphenoxy)propyl, 3-(4-(2-(4-(4-hydroxyphenylsulfonyl)phenoxy) dodecanamido)phenyl)propyl, 2-ethoxytridecyl, trifluoromethyl, cyclopentyl, 3-(2,4-di-t-amylphenoxy) propyl; aryl (for example phenyl, 4-t-butylphenyl, 2,4-di-t-amylphenyl or 4-tetradecanamidophenyl); heterocyclyl (for example 2-furyl, 2-thienyl, 2-pyrimidinyl or 2-benzothiazolyl); cyano; hydroxyl, nitro; carboxyl; amino;

alkoxy (for example methoxy, ethoxy, 2-methoxyethoxy; 2-dodecylethoxy, 2-methanesulfonylethoxy); aryloxy (for example phenoxy, 2-methylphenoxy, 4-t-butylphenoxy, 3-nitrophenoxy, 3-t-butyloxycarbamoylphenoxy or 3-methoxycarbamoyl); acylamino (for example acetamido, benzamido, tetradecanamido, 2-(2',4-di-t-amylphenoxy) butanamido, 4-(3-t-butyl-4-hydroxyphenoxy)butanamido, 2-(4-(4-hydroxyphenylsulfonyl)phenoxy)decanamido or methylbutylamino); anilino (for example phenylamino, 2-chloroanilino, 2-chloro-5-tetradecanaminoanilino, 2-chloro-5-dodecyloxycarbonylanilino, N-acetylanilino, 2-chloro-5-(alpha-(3-t-butyl-4-hydroxyphenoxy) dodecanamidoanilino); ureido (for example phenylureido, methylureido or N,N-dibutylureido); sulfamoylamino (for example N,N-dipropylsulfamoylamino or N-methyl-N-decylsulfamoylamino); alkylthio (for example methylthio, octylthio, tetradecylthio, 2-phenoxyethylthio, 3-phenoxypropylthio or 3-(4-t-butylphenoxy)propylthio); arylthio (for example phenylthio, 2-butoxy-5-t-octylphenylthio, 3-pentadecylphenylthio, 2-carboxyphenylthio or 4-tetradecanamidophenylthio); alkoxycarbonylamino (for example methoxycarbonylamino or tetradecyloxycarbonylamino); sulfonamido (for example methanesulfonamido, hexadecanesulfonamido, benzenesulfonamido, p-toluenesulfonamido, octadecanesulfonamido or 2-methoxy-5-t-butylbenzenesulfonamido); carbamoyl (for example N-ethylcarbamoyl, N,N-dibutylcarbamoyl, N-(2-dodecyloxyethyl)carbamoyl, N-methyl-N-dodecylcarbamoyl or N-(3-(2,4-di-t-amylphenoxy)propyl)carbamoyl); sulfamoyl (for example N-ethylsulfamoyl, N,N-dipropylsulfamoyl, N-2-(dodecyloxyethyl)sulfamoyl, N-ethyl-N-dodecylsulfamoyl or N,N-diethylsulfamoyl); sulfonyl (for example methanesulfonyl, octanesulfonyl, benzenesulfonyl or toluenesulfonyl); alkoxycarbonyl (for example methoxycarbonyl, butoxycarbonyl, dodecyloxycarbonyl or octadecyloxycarbonyl); heterocyclyloxy (for example 1-phenyltetrazol-5-oxy or 2-tetrahydropyranyloxy); azo (for example phenylazo, 4-methoxyphenylazo, 4-pivaloylaminophenylazo or 2-hydroxy-4-propanoylphenylazo); acyloxy (for example acetoxy); carbamoyloxy (for example N-methylcarbamoyloxy or N-phenylcarbamoyloxy); silyloxy (for example trimethylsilyloxy or dibutylmethylsilyloxy); aryloxycarbonylamino (for example phenoxycarbonylamino); imido (for example N-succinimido, N-phthalimido or 3-octadecenylsuccinimido); heterocyclylthio (for example 2-benzothiazolylthio, 2,4-diphenyloxy-1,3,5-triazole-6-thio or 2-pyridylthio); sulfinyl (for example dodecanesulfmyl, 3-pentadecylphenylsulfinyl or 3-phenoxypropylsulfinyl); phosphonyl (for example phenoxyphosphonyl, octyloxyphosphonyl or phenylphosphonyl); aryloxycarbonyl (for example phenoxycarbonyl); acyl (for example acetyl, 3-phenylpropanoyl, benzoyl or 4-dodecyloxybenzoyl); or azolyl (for example imidazolyl, pyrazolyl or 3-chloropyrazol-1-yl).

These substituents may be further substituted, for example by halogen or by an organic radical bonded via a C, O, N or S atom.

Preferred groups $R_{11}$ are alkyl, aryl, alkoxy, aryloxy, alkylthio, ureido, urethane and acylamino groups.

$R_{12}$ may be as defined for $R_{11}$ and is preferably hydrogen, alkyl, aryl, a heterocyclic ring, alkoxycarbonyl, carbamoyl, sulfamoyl, sulfinyl, acyl or cyano.

$R_{13}$ may be as defined for $R_{11}$ and is preferably hydrogen, alkyl, aryl, a heterocyclic ring, alkoxy, aryloxy, alkylthio, arylthio, alkoxycarbonyl, carbamoyl or acyl, in particular alkyl, aryl, a heterocyclic ring, alkylthio or arylthio.

Q is hydrogen or a leaving group, such as halogen, alkoxy, aryloxy, acyloxy, alkyl- or arylsulfonyloxy, acylamino, alkyl- or arylsulfonamido, alkoxycarbonyloxy, aryloxycarbonyloxy, alkyl-, aryl- or heterocyclyl-S-carbamoylamino, a 5- or 6-membered, nitrogen-containing heterocyclic radical, imido or arylazo. These groups may be further substituted as indicated for $R_{11}$.

Q is preferably halogen (for example fluorine, chlorine or bromine); alkoxy (for example ethoxy, dodecyloxy, methoxyethylcarbamoylmethoxy, carboxypropoxy, methylsulfonylethoxy, or ethoxycarbonylmethoxy); aryloxy (for example 4-methylphenoxy, 4-chlorophenoxy, 4-methoxyphenoxy, 4-carboxyphenoxy, 3-ethoxycarboxyphenoxy, 3-acetylaminophenoxy or 2-carboxyphenoxy); acyloxy (for example acetoxy, tetradecanoyloxy or benzoyloxy); alkyl- or arylsulfonyloxy (for example methanesulfonyloxy or toluenesulfonyloxy); acylamino (for example dichloroacetylamino or heptafluorobutyrylamino); alkyl- or arylsulfonamido (for example methanesulfonamido, trifluoromethanesulfonamido or p-toluenesulfonamido); alkoxycarbonyloxy (for example ethoxycarbonyloxy or benzyloxycarbonyloxy); aryloxycarbonyloxy (for example phenoxycarbonyloxy); alkyl-, aryl- or heterocyclyl-S-(for example dodecylthio, 1-carboxydodecylthio, phenylthio, 2-butoxy-5-t-octylphenylthio or tetrazolylthio); carbamoylamino (for example N-methylcarbamoylamino or N-phenylcarbamoylamino); a 5- or 6-membered, nitrogen-containing ring (for example imidazolyl, pyrazolyl, triazolyl, tetrazolyl or 1,2-dihydro-2-oxo-1-pyridyl); imido (for example succinimido or hydantoinyl); or arylazo (for example phenylazo or 4-methoxyphenylazo).

Q may alternatively form corresponding bis-compounds by condensation of 4 equivalents of coupler with an aldehyde or ketone. Furthermore, Q may contain photographically active groups, such as development inhibitors or development accelerators. Q is preferably halogen, alkoxy, aryloxy, alkyl- or arylthio, or a 5- or 6-membered, nitrogen-containing, heterocyclic group which is bonded to the coupling site via a nitrogen atom.

Pyrazolotetrazoles are described in JP-A 85/33 552; pyrazolopyrazoles in JP-A 85/43 695; pyrazoloimidazoles in JP-A 85/35 732, JP-A 86/18 949 and U.S. Pat. No. 4,500, 630; pyrazolotriazoles in JP-A 85/186 567, JP-A 86/47 957, JP-A 85/215 687, JP-A 85/197 688, JP-A 85/172 982, EP-A 119 860, EP-A 173 256, EP-A 178 789, EP-A 178 788 and in Research Disclosure 84/24 624.

Further pyrazoloazole magenta couplers are described in: JP-A 86/28 947, JP-A 85/140 241, JP-A 85/262 160, JP-A 85/213 937, JP-A 87/278 552, JP-A 87/279 340, JP-A 88/100 457, EP-A 177 765, EP-A 176 804, EP-A 170 164, EP-A 164 130, EP-A 178 794, DE-A 3 516 996, DE-A 3 508 766 and Research Disclosure 81/20 919, 84/24 531 and 85/25 758.

Examples of suitable couplers of this type are:

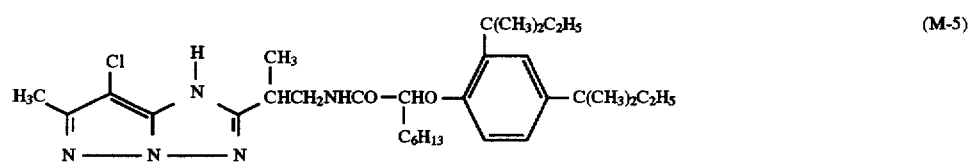

(M-5)

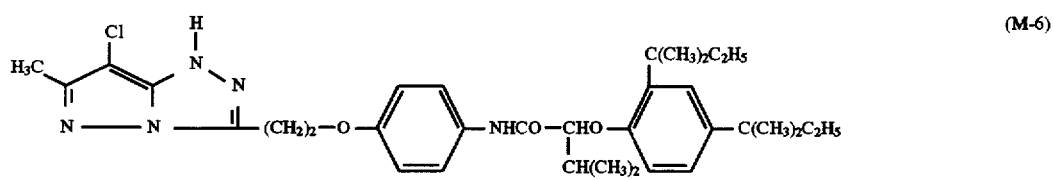

(M-6)

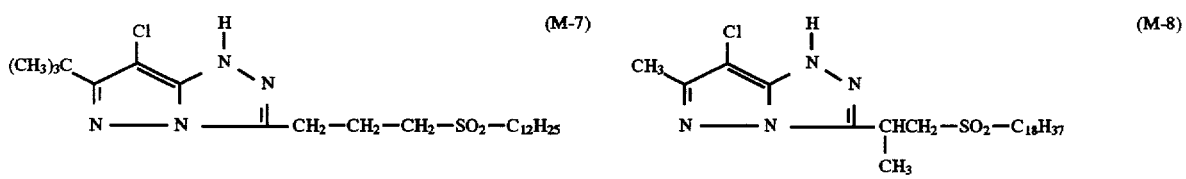

(M-7) (M-8)

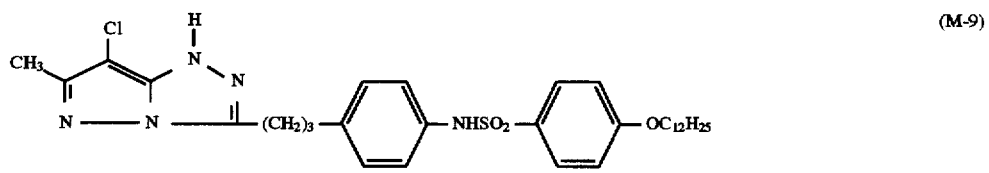

(M-9)

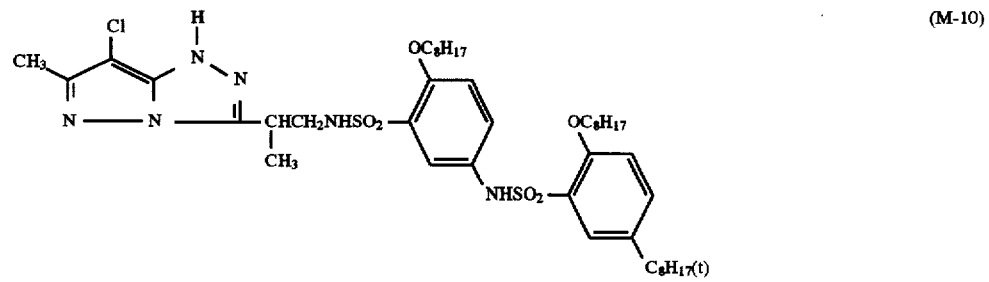

(M-10)

-continued
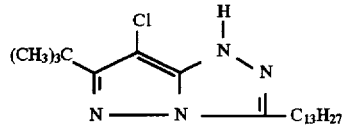
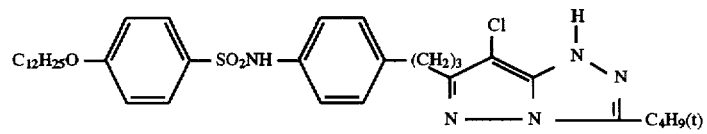
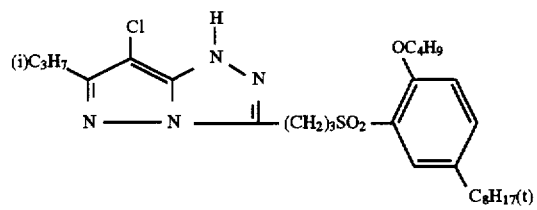
(M-11)
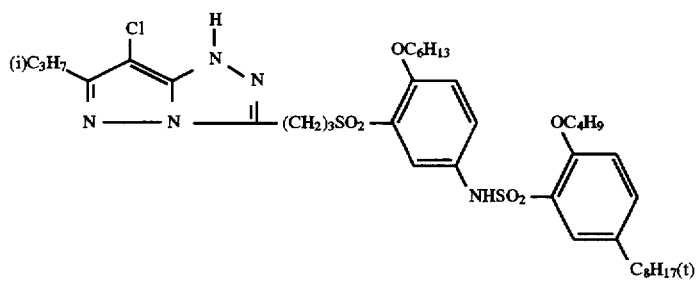
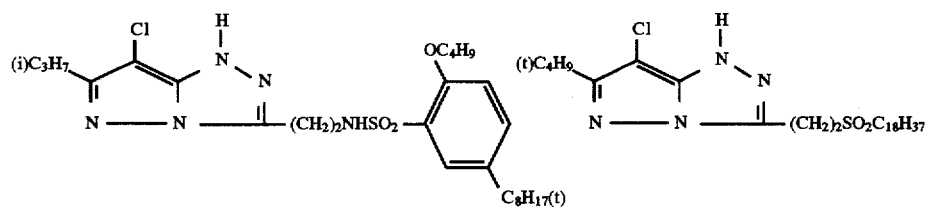
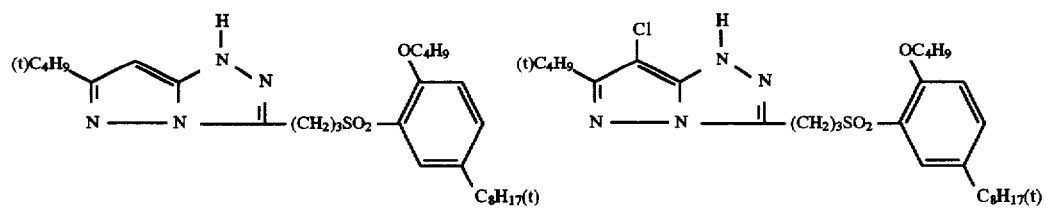
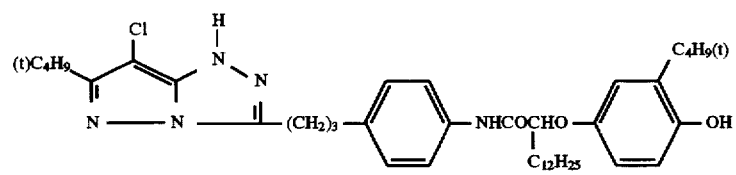
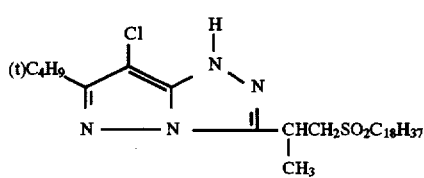

-continued
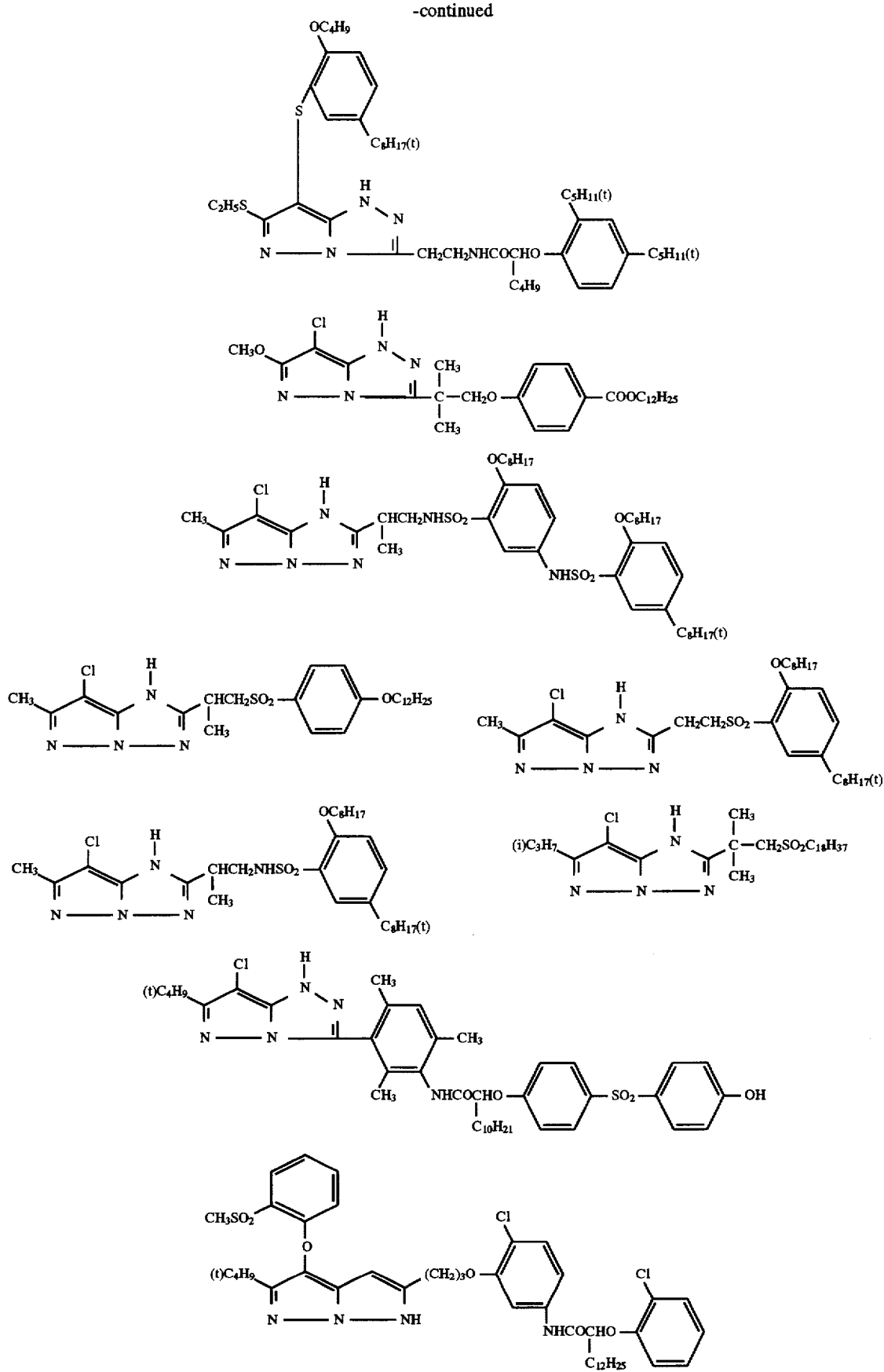

-continued
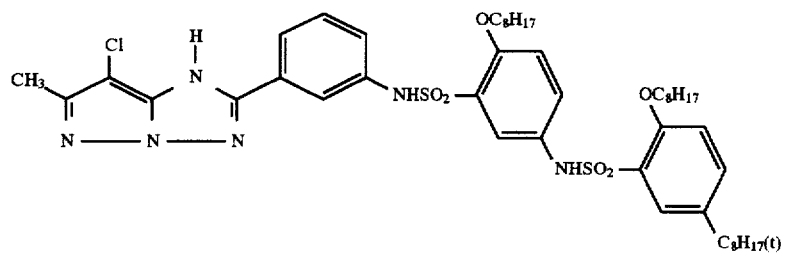
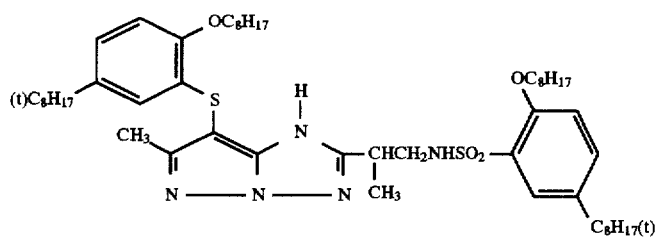
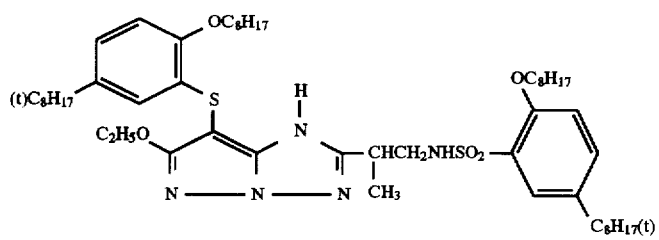
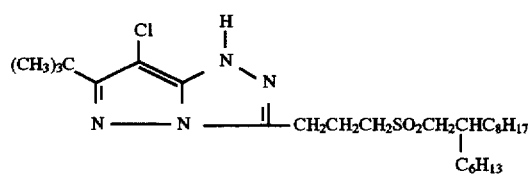
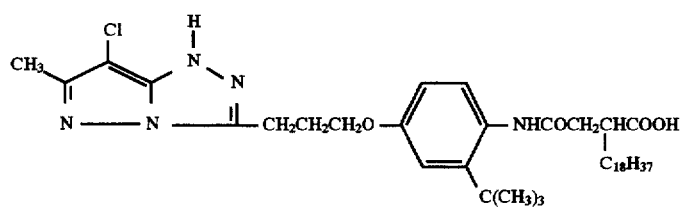
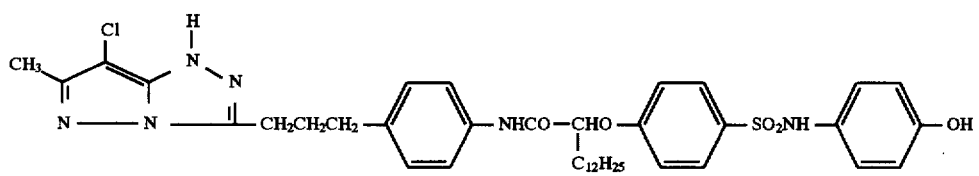
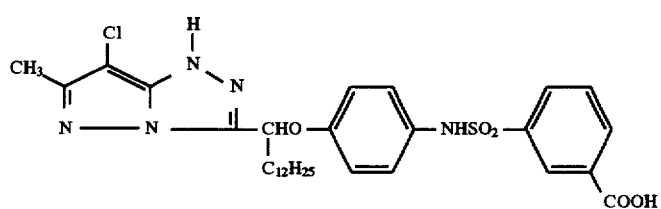

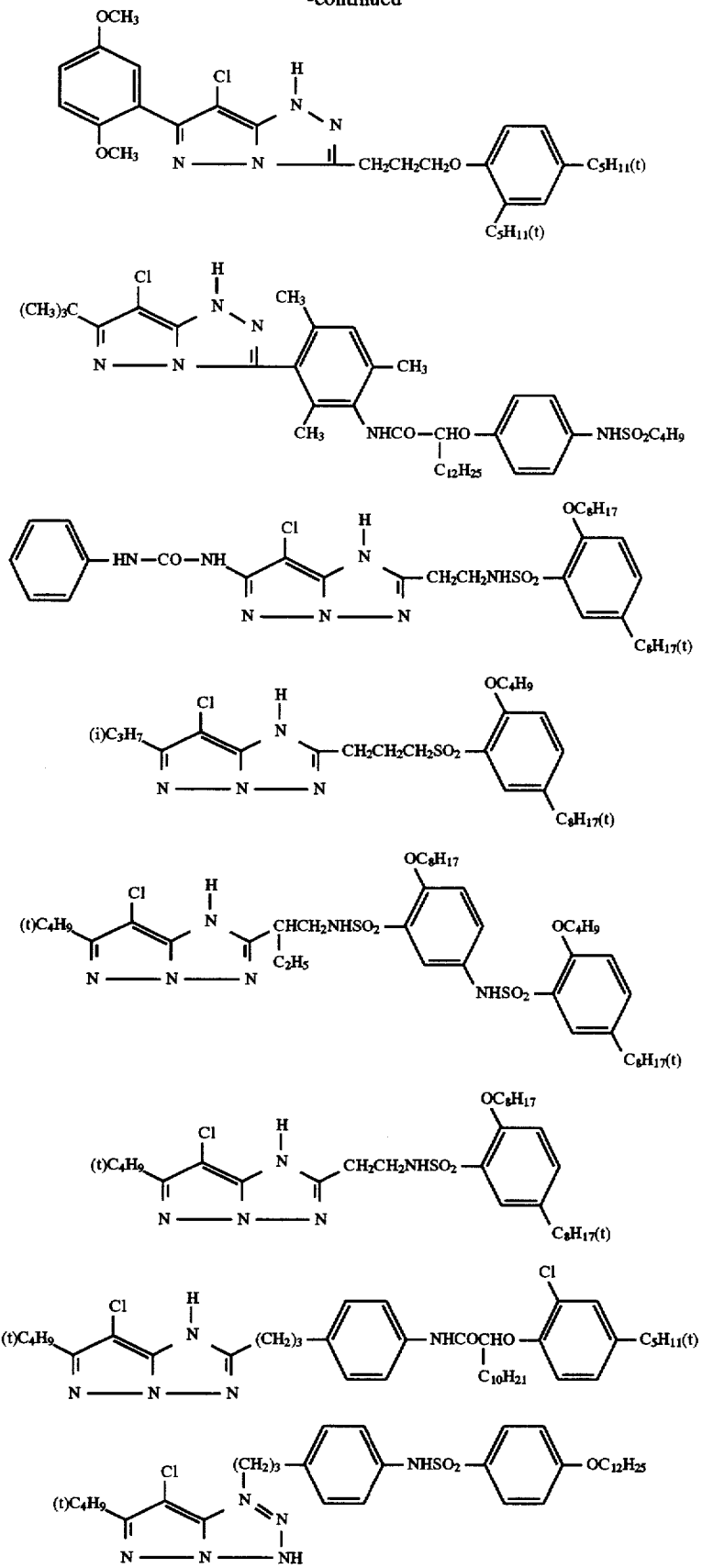

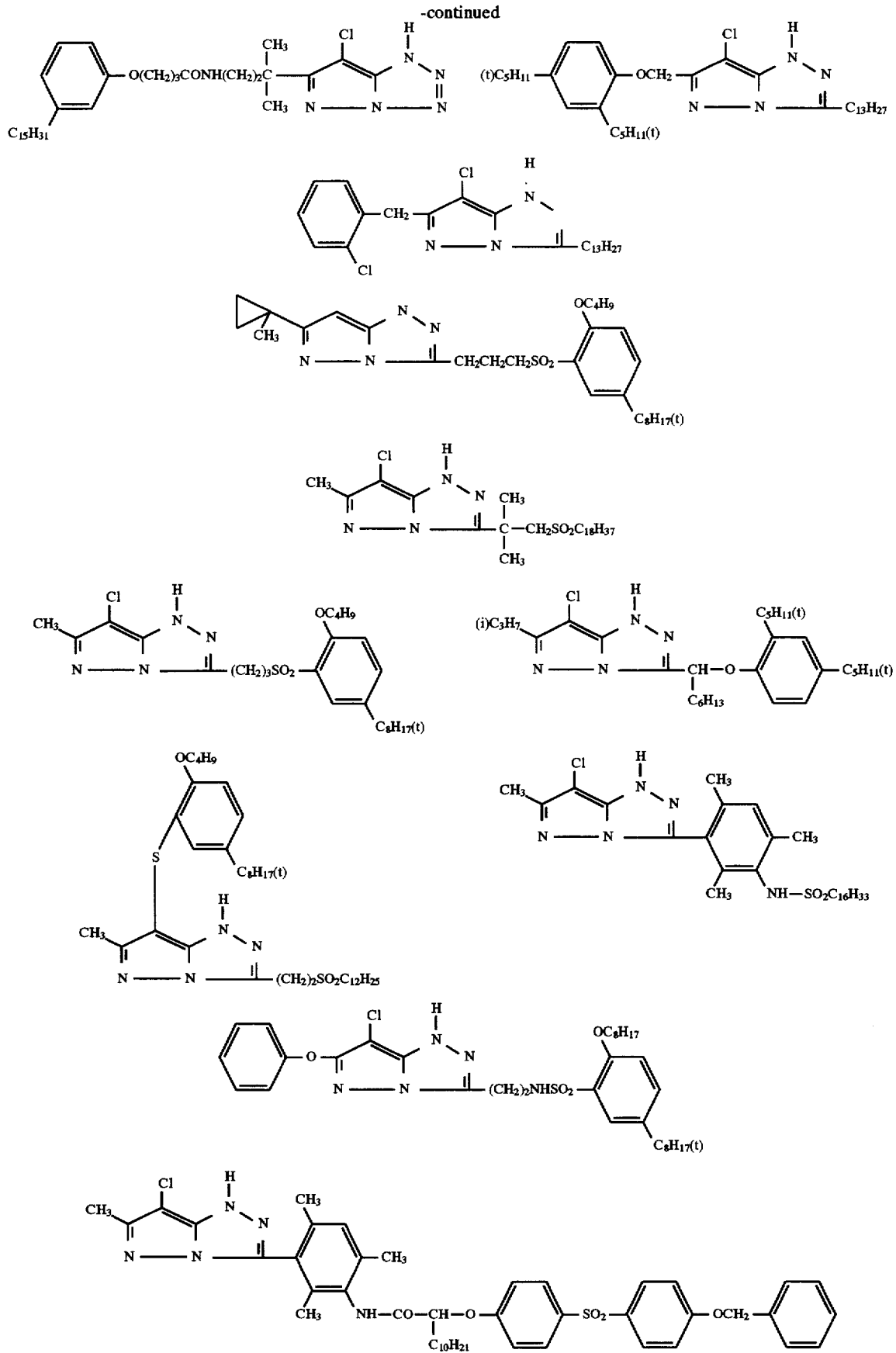

-continued
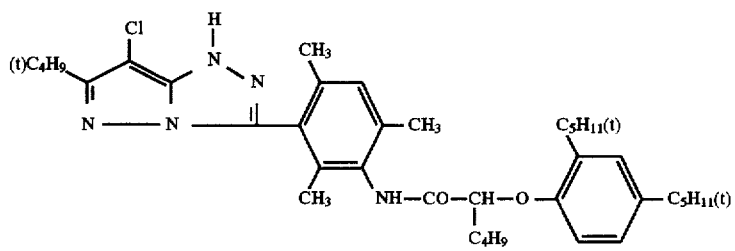
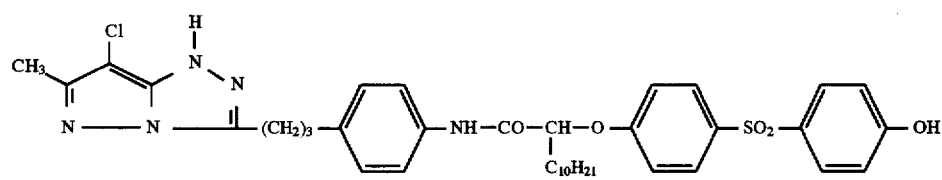
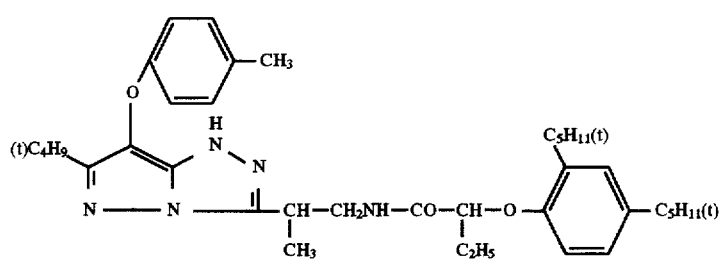
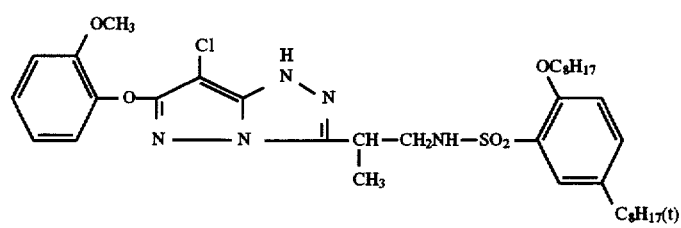
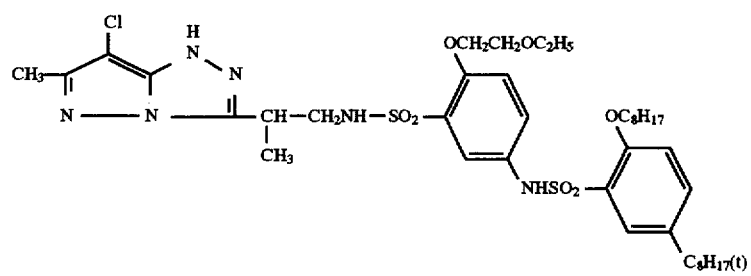
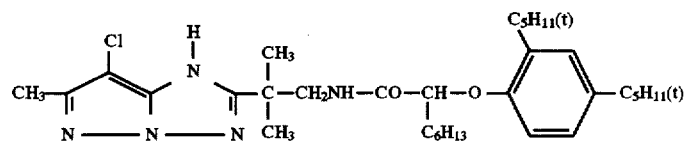
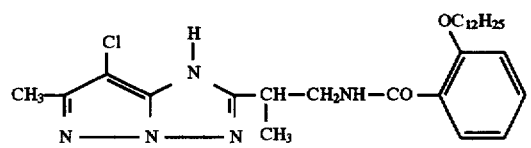
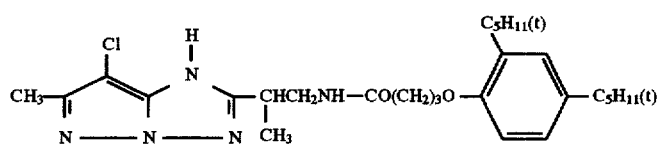

-continued

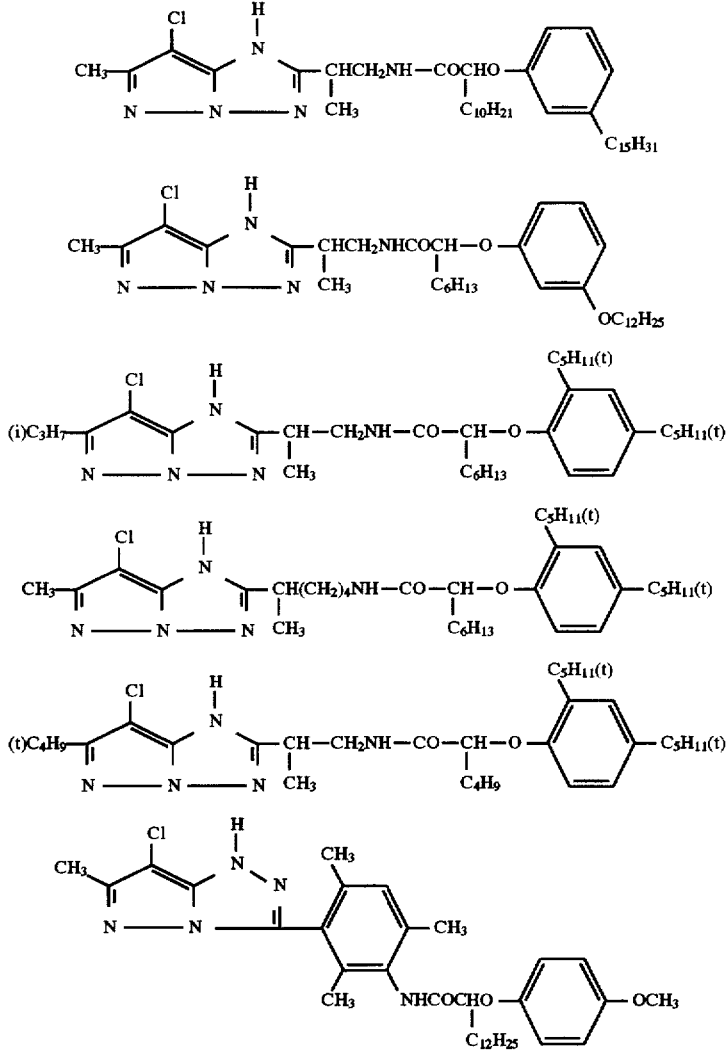

Yellow couplers which can be used in the material according to the invention are preferably compounds of the formula A

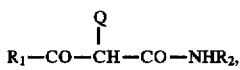

(A)

in which $R_1$ is alkyl or aryl, $R_2$ is aryl and Q is hydrogen or a group which can be eliminated by reaction with the oxidized developer.

A group of yellow couplers comprises the compounds of the formula A in which $R_1$ is t-butyl and $R_2$ is a group of the formula

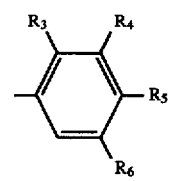

in which $R_3$ is hydrogen, halogen, alkyl or alkoxy, and $R_4$, $R_5$ and $R_6$ are hydrogen, halogen, alkyl, alkenyl, alkoxy, aryl, carboxyl, alkoxycarbonyl, carbamoyl, sulfonyl, sulfamoyl, alkylsulfonamido, acylamino, ureido or amino.

Preferably, $R_3$ is chlorine, $R_4$ and $R_5$ are hydrogen and $R_6$ is an acylamino group. This group also includes the compounds of the formula

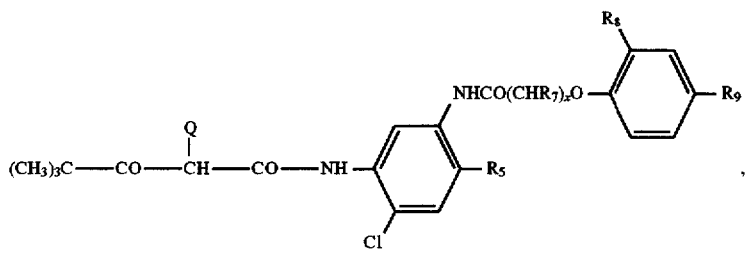

in which x is 0–4, $R_7$ is hydrogen or alkyl, and $R_8$ and $R_9$ are alkyl.

Another group of yellow couplers conforms to the formula B

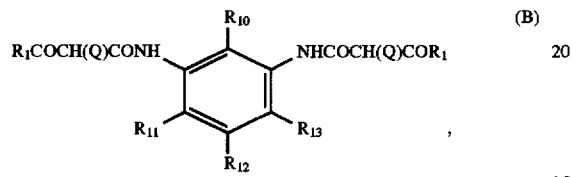

in which $R_{10}$ is hydrogen, halogen or alkoxy, $R_{11}$, $R_{12}$ and $R_{13}$ are hydrogen, halogen, alkyl, alkenyl, alkoxy, aryl, carboxyl, alkoxycarbonyl, carbamoyl, sulfonyl, sulfamoyl, sulfonamido, acylamino, ureido or amino, and $R_1$ and Q are as defined above.

This group includes compounds of the formula B in which $R_1$ is t-butyl, $R_{10}$ is chlorine, $R_{11}$ and $R_{13}$ are hydrogen, and $R_{12}$ is alkoxycarbonyl.

In the compounds of the formulae A and B, leaving group Q may be hydrogen or a heterocyclic group

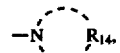

in which $R_{14}$ is a divalent organic group which supplements the ring to make up a 4–7-membered ring, or Q is an —$OR_{15}$ group in which $R_{15}$ is alkyl, aryl, acyl or a heterocyclic radical.

Typical examples of customary yellow couplers are the compounds of the formulae below:

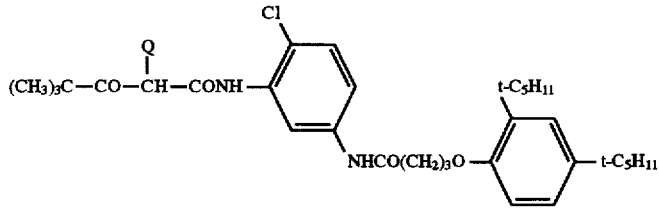

a) Q = 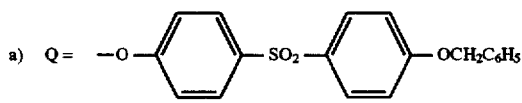

b) Q = 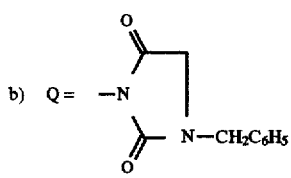

c) Q = 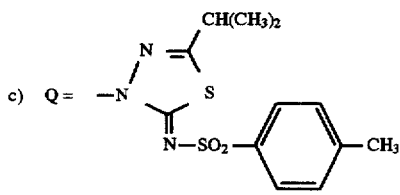

d) Q = 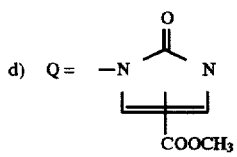

-continued
e) Q= 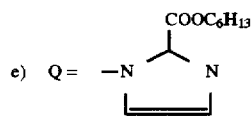
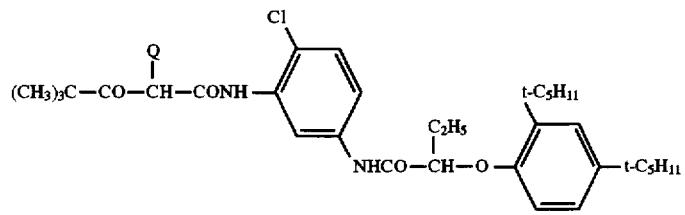
f) Q= 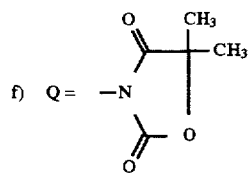   g) Q= 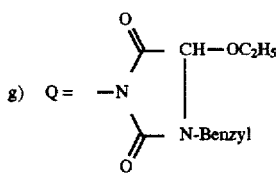
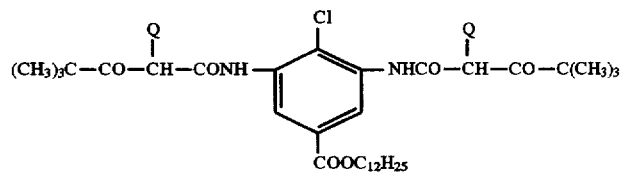
h) Q= 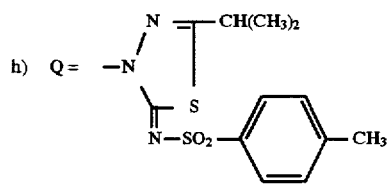
Further examples of yellow couplers are given in U.S. Pat. Nos. 2,407,210, 2,778,658, 2,875,057, 2,908,513, 2,908,573, 3,227,155, 3,227,550, 3,253,924, 3,265,506, 3,277,155, 3,408,194, 3,341,331, 3,369,895, 3,384,657, 3,415,652, 3,447,928, 3,551,155, 3,582,322, 3,725,072, 3,891,445, 3,933,501, 4,115,121, 4,401,752 and 4,022,620, in DE-A 1 547 868, 2 057 941, 2 162 899, 2 163 813, 2 213 461, 2 219 917, 2 261 361, 2 261 362, 2 263 875, 2 329 587, 2 414 006 and 2 422 812, in GB-A 1 425 020 and 1 077 874 and in JP-A 88/123 047 and in EP-A 447 969.
Typical and preferred yellow couplers conform to the formnulae:
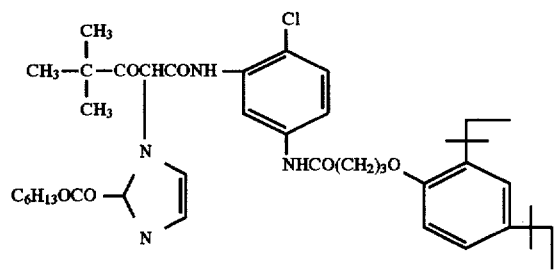 (Y-1)

-continued
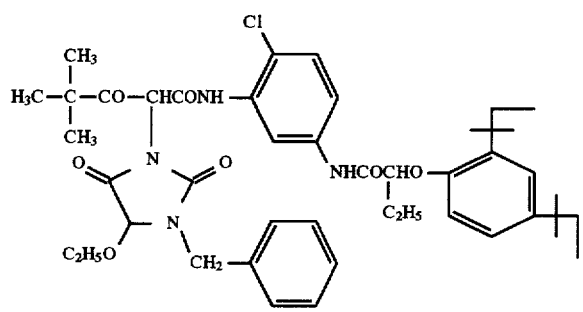
(Y-2)
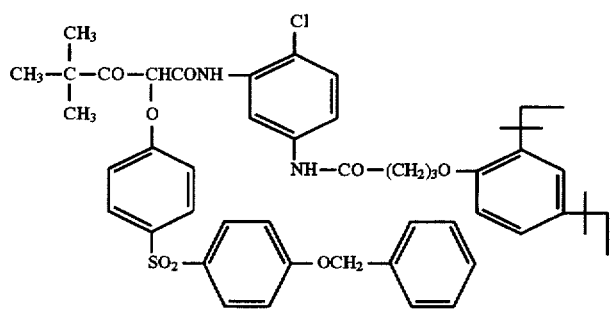
(Y-3)
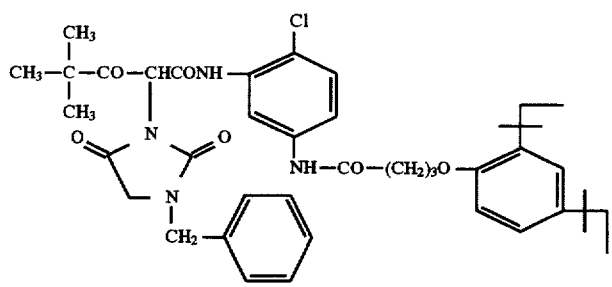
(Y-4)
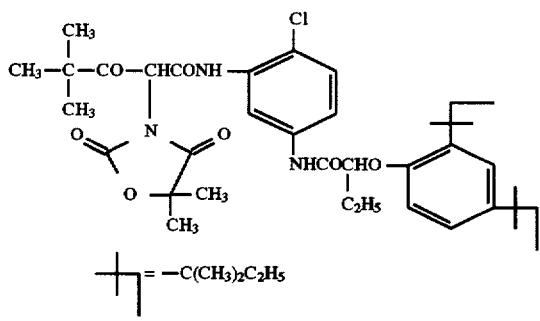
(Y-5)
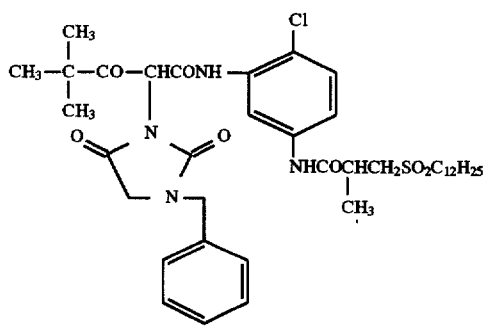
(Y-6)

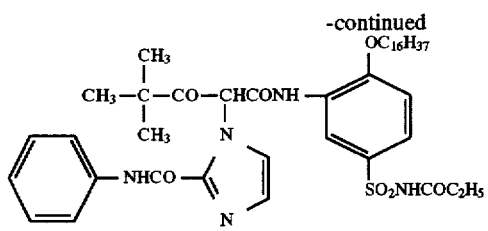
(Y-7)

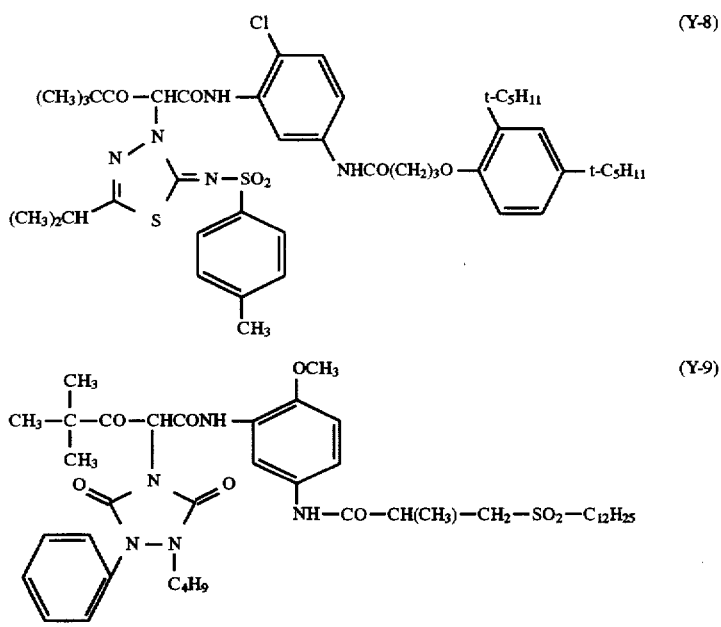
(Y-8)

(Y-9)

Cyan couplers may be, for example, derivatives of phenol, of 1-naphthol or of pyrazoloquinazolone. Preference is given to structures of the formula E

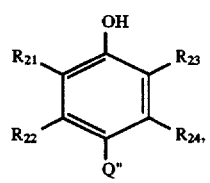
(E)

in which $R_{21}$, $R_{22}$, $R_{23}$ and $R_{24}$ are hydrogen, halogen, alkyl, carbamoyl, amino, sulfonamido, phosphoramido or ureido. $R_{21}$ is preferably H or Cl, $R_{22}$ is preferably an alkyl or amino group. $R_{23}$ is preferably an amino group and $R_{24}$ is preferably hydrogen. Q" is hydrogen or a leaving group which is eliminated during the reaction with the oxidized developer. A detailed list of cyan couplers is given in U.S. Pat. No. 4,456,681.

Further examples of cyan couplers are given in the following: U.S. Pat. Nos. 2,369,929, 2,423,730, 2,434,272, 2,474,293, 2,521,293, 2,521,908, 2,698,794, 2,706,684, 2,772,162, 2,801,171, 2,895,826, 2,908,573, 3,034,892, 3,046,129, 3,227,550, 3,253,294, 3,311,476, 3,386,301, 3,419,390, 3,458,315, 3,476,560, 3,476,563, 3,516,831, 3,560,212, 3,582,322, 3,583,971, 3,591,383, 3,619,196, 3,632,347, 3,652,286, 3,737,326, 3,758,308, 3,839,044, 3,880,661, 4 004,929, 4,124,396, 4,333,999, 4,463,086, 4,456,681, 4,873,183 and 4,923,791 and in EP-A 354 549 and EP-A 398 664.

The red-sensitive silver-halide emulsion layer of the material according to the invention preferably contains a cyan coupler of the formula

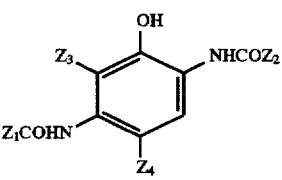
(E-1)

and/or of the formula

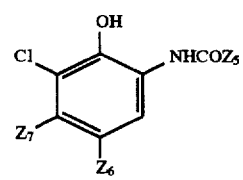
(E-2)

in which $Z_1$ is alkyl or aryl, $Z_2$ is alkyl, cycloalkyl, aryl, a heterocyclic group or a ballast group, $Z_3$ is hydrogen or halogen, $Z_1$ and $Z_3$ together can form a ring, and $Z_4$ is hydrogen or a leaving group, and $Z_5$ is a ballast group, $Z_6$ is hydrogen or a leaving group and $Z_7$ is alkyl.

Examples of customary cyan couplers are the following:

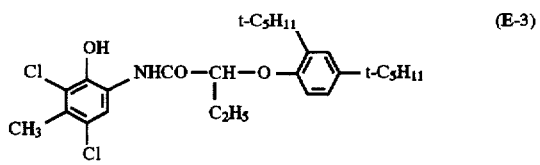
(E-3)

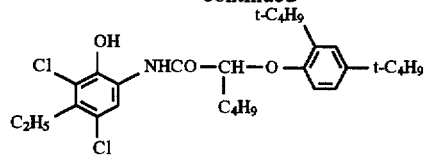
(E-4)

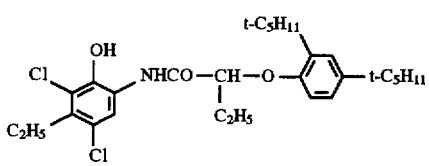
(E-5)

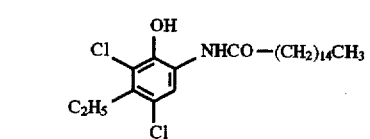
(E-6)

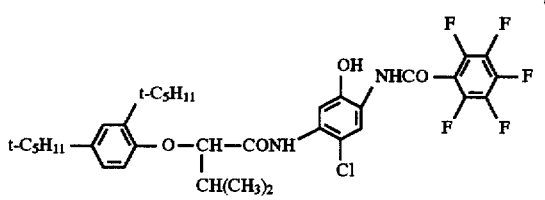
(E-7)

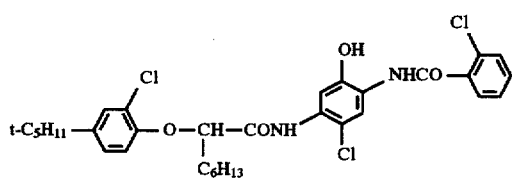
(E-8)

The colour developers usually used for colour-photographic materials are p-dialkylaminoanilines. Examples of these are 4-amino-N,N-diethylaniline, 3-methyl-4-amino-N,N-diethylaniline, 4-amino-N-ethyl-N-α-hydroxyethylaniline, 3-methyl-4-amino-N-ethyl-N-α-hydroxyethylaniline, 3-methyl-4-amino-N-ethyl-N-α-hydroxyethylaniline, 3-methyl-4-amino-N-ethyl-N-α-methanesulfonamidoethylaniline, 3-methyl-4-amino-N-ethyl-N-α-methoxyethylaniline, 3-α-methanesulfonamidoethyl-4-amino-N,N-diethylaniline, 3-methoxy-4-amino-N-ethyl-N-α-hydroxyethylaniline, 3-methoxy-4-amino-N-ethyl-N-α-methoxyethylaniline, 3-acetamido-4-amino-N,N-diethylaniline, 4-amino-N,N-dimethylaniline, N-ethyl-N-α-[α'-(α"-methoxyethoxy)ethoxy]ethyl-3-methyl-4-aminoaniline, N-ethyl-N-α-(α'-methoxyethoxy)ethyl-3-methyl-4-aminoaniline, and the salts of these compounds, for example sulfates, hydrochlorides or toluenesulfonates.

The compounds of the formulae (Ia), (Ib) and (II) according to the invention, the magenta couplers and other colour couplers can be incorporated into the colour-photographic material in a known manner, for example into silver-halide emulsions which contain gelatin and/or other binders. They are used, for example, in silver-bromide, silver-chloride or silver-iodide emulsions or in emulsions which contain mixtures of silver halides, such as silver bromide/iodide or silver-chloride/bromide emulsions.

The compounds of the formulae (Ia), (Ib) and (II) according to the invention can be incorporated into the colour-photographic material together with the magenta coupler and if desired further additives by predissolving them in high-boiling organic solvents. Preference is given to solvents which boil higher than 160° C. Typical examples of these solvents are the esters of phthalic acid, phosphoric acid, citric acid, benzoic acid or fatty acids, and alkylamides and phenols.

A low-boiling solvent is usually used in addition in order to simplify incorporation of the additives into the colour-photographic material. Examples of such solvents are esters, for example ethyl acetate, alcohols, for example butanol, ketones, for example methyl isobutyl ketone, chlorinated hydrocarbons, for example methylene chloride, and amides, for example dimethylformamide. If the additives are themselves liquid, they can also be incorporated into the photographic material without the assistance of solvents.

The compounds according to the invention may if desired be dispersed in the gelatin layer as oil.

Further details on high-boiling solvents which can be used are given in the publications below:

Phosphates: GB-A 791 219, BE-A 755 248, JP-A 76/76 739, 78/27 449, 78/218 252, 78/97 573, 79/148 133, 82/216 177, 82/93 323 and 83/216 177 and EP-A 265 296.

Phthalates: GB-A 791 219, JP-A 77/98 050, 82/93 322, 82/216 176, 82/218 251, 83/24 321, 83/45 699 and 84/79 888.

Amides: GB-A 791 129, JP-A 76/105 043, 77/13 600, 77/61 089, 84/189 556, 87/239 149, EP-A 270 341 and WO 88/00 723.

Phenols: GB-A 820 329, FR-A 1 220 657, JP-A 69/69 946, 70/3818, 75/123 026, 75/82 078, 78/17 914, 78/21 166, 82/212 114 and 83/45 699.

Other oxygen-containing compounds: U.S. Pat. Nos. 3,748,141, 3,779,765, JP-A 73/75 126, 74/101 114, 74/10 115, 75/101 625, 76/76 740, 77/61 089, EP-A 304 810 and BE-A 826 039.

Other compounds: JP-A 72/115 369, 72/130 258, 73/127 521, 73/76 592, 77/13 193, 77/36 294, 79/95 233, 91/2748, 83/105 147 and Research Disclosure 82/21 918.

The amount of high-boiling solvent is, for example, in the range from 50 mg to 2 g per $m^2$ of base, preferably from 200 mg to 1 g per $m^2$.

The photographic layers may furthermore contain colour cast inhibitors. These prevent colour casts being formed, due, for example, to reaction of the coupler with unintentionally oxidized developer or with by-products of the colour-formation process. Colour cast inhibitors of this type are usually hydroquinine derivatives, but may also be derivatives of aminophenols, of gallic acid or of ascorbic acid. Typical examples of these inhibitors are given in the publications below: U.S. Pat. Nos. 2,360,290, 2,336,327, 2,403,721, 2,418,613, 2,675,314, 2,701,197, 2,704,713, 2,728,659, 2,732,300, 2,735,365; EP-A 124 877, EP-A 277 589, EP-A 338 785; JP-A 75/92 988, 75/92 989, 75/93 928, 75/110 337, 84/5247 and 77/146 235.

Photographic layers may also contain DIR couplers (DIR denotes Development Inhibition Release), which form colourless compounds with the oxidized developer. They are added to improve the sharpness and grain of the colour prints.

The photographic layers in the material according to the invention may also contain UV absorbers. These filter out the UV light and thus protect the dyes, the couplers and other components against photodegradation. Examples of such UV absorbers are 2-(2-hydroxyphenyl)benzotriazoles, 2-hydroxyphenyl-1,3,5-triazines, 2-hydroxybenzophenones, salicylic acid esters, acrylonitrile derivatives or thiazolines. UV absorbers of this type are described in greater detail, for example, in the following publications: U.S. Pat. Nos. 3,314,794, 3,352,681, 3,705,805, 3,707,375, 4,045,229, 3,700,455, 3,533,794, 3,698,907, 3,705,805, 3,738,837 and JP-A 71/2784. Preferred UV absorbers are the 2-(2-hydroxyphenyl)benzotriazoles (HBTs) of the formula

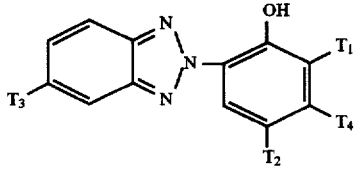

in which $T_1$, $T_2$ and $T_3$, independently of one another, are hydrogen, halogen, alkyl, alkyl which is substituted by a carboxylate group, alkoxy, aryloxy, hydroxyl or acyloxy, and $T_4$ is hydrogen, alkoxy, aryloxy or acyloxy.

Particular preference is given to HBT compounds which are liquid at room temperature.

Examples of preferred HBT compounds are:

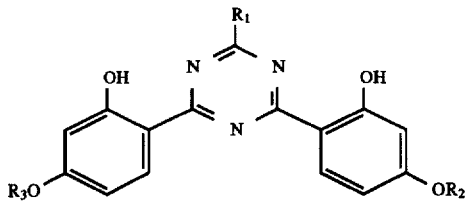

| HBT No. | $T_1$ | $T_4$ | $T_3$ |
|---|---|---|---|
| HBT-1 | H | $CH_3$ | H |
| HBT-2 | H | $C(CH_3)_3$ | H |
| HBT-3 | $C(CH_3)_3$ | $CH_3$ | Cl |
| HBT-4 | $C(CH_3)_3$ | $C(CH_3)_3$ | Cl |
| HBT-5 | $C(CH_3)_2C_2H_5$ | $C(CH_3)_2C_2H_5$ | H |
| HBT-6 | $CH(CH_3)C_2H_5$ | $C(CH_3)_3$ | H |
| HBT-7 | $C(CH_3)_2$—Ph | $C(CH_3)_2$—Ph | H |
| HBT-8 | $C(CH_3)_3$ | $CH_2CH_2COOC_8H_{17}$ (isomers) | Cl |
| HBT-9 | $C(CH_3)_3$ | $CH_2CH_2COOC_8H_{17}$ (isomers) | H |
| HBT-10 | $C_{12}H_{25}$ (isomers)* | $CH_3$ | H |

*Principal product

Other preferred UV absorbers are 2-hydroxyphenyl-1,3,5-triazines of the formula

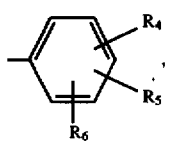

in which $R_1$ is a group of the formula

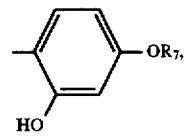

where $R_4$, $R_5$ and $R_6$, independently of one another, are hydrogen, $C_1$–$C_{12}$alkyl or halogen, or $R_1$ is a group of the formula and $R_2$, $R_3$ and $R_7$, independently of one another, are monovalent organic radicals. $R_2$, $R_3$ and $R_7$ are preferably, independently of one another, a radical $CH_2CH(OR_8)CH_2OR_9$, where $R_8$ is hydrogen or acetyl, and $R_9$ is $C_1$–$C_{18}$alkyl.

The photographic layers may also contain phenolic compounds which act as light stabilizers for the colour image and as colour cast inhibitors. They may be present in a light-sensitive layer (colour layer) or in an intermediate layer, alone or together with other additives. Such compounds are described in greater detail, for example, in the publications below: U.S. Pat. Nos. 3,700,455, 3,591,381, 3,573,052, 4,030,931, 4,174,220, 4,178,184, 4,228,235, 4,279,990, 4,346,165, 4,366,226, 4,447,523, 4,528,264, 4,581,326, 4,562,146, 4,559,297, GB-A 1 309 277, 1 547 302, 2 023 862, 2 135 788, 2 139 370, 2 156 091; DE-A 2 301 060, 2 347 708, 2 526 468, 2 621 203, 3 323 448; DD-A 200 691, 214 468; EP-A 106 799, 113 124, 125 522, 159 912, 161 577, 164 030, 167 762, 176 845, 246 766, 320 776; JP-A 74/134 326, 76/127 730, 76/30 462, 77/3822, 77/154 632, 78/10 842, 79/48 535, 79/70 830, 79/73 032, 79/147 038, 79/154 325, 79/155 836, 82/142 638, 83/224 353, 84/5246, 84/72 443, 84/87 456, 84/192 246, 84/192 247, 84/204 039, 84/204 040, 84/212 837, 84/220 733, 84/222 836, 84/228 249, 86/2540, 86/8843, 86/18 835, 86/18 836, 87/11 456, 87/42 245, 87/62 157, 86/6652, 89/137 258 and in Research Disclosure 79/17 804.

The photographic layers may also contain certain phosphorus(III) compounds, in particular phosphites and phosphonites. These act as light stabilizers for the colour images and as dark-storage stabilizers for magenta couplers. They are preferably added to the high-boiling solvents together with the coupler. Phosphorus(III) compounds of this type are described in greater detail, for example, in the publications below: U.S. Pat. No. 4,407,935, U.S. Pat. No. 4,436,811, U.S. Pat. No. 4,956,406, EP-A 181 289, JP-A 73/32 728, JP-A 76/1420 and JP-A 55/66 741.

The photographic layers may also contain organometallic complexes which are light stabilizers for the colour images, in particular for the magenta dyes. Such compounds and combinations thereof with other additives are described in greater detail, for example, in the publications below: U.S. Pat. Nos. 4,050,938, 4,239,843, 4,241,154, 4,242,429, 4,241,155, 4,242,430, 4,273,854, 4,246,329, 4,271,253, 4,242,431, 4,248,949, 4,245,195, 4,268,605, 4,246,330, 4,269,926, 4,245,018, 4,301,223, 4,343,886, 4,346,165, 4,590,153; JP-A 81/167 138, 81/168 652, 82/30 834, 82/161 744; EP-A 137 271, 161 577, 185 506; DE-A 2 853 865.

The photographic layers may also contain hydroquinone compounds. These act as light stabilizers for the colour couplers and for the colour images and as scavengers of oxidized developer in the intermediate layers. They are used in particular in the magenta layer. Hydroquinone compounds of this type and combinations thereof with other additives are described in greater detail, for example, in the publications below: U.S. Pat. Nos. 2,360,290, 2,336,327, 2,403,721, 2,418,613, 2,675,314, 2,701,197, 2,710,801, 2,732,300, 2,728,659, 2,735,765, 2,704,713, 2,937,086, 2,816,028, 3,582,333, 3,637,393, 3,700,453, 3,960,570, 3,935,016, 3,930,866, 4,065,435, 3,982,944, 4,232,114, 4,121,939, 4,175,968, 4,179,293, 3,591,381, 3,573,052, 4,279,990, 4,429,031, 4,346,165, 4,360,589, 4,346,167, 4,385,111, 4,416,978, 4,430,425, 4,277,558, 4,489,155, 4,504,572, 4,559,297, FR-A 885 982; GB-A 891 158, 1 156 167, 1 363 921, 2 022 274, 2 066 975, 2 071 348, 2 081 463, 2 117 526, 2 156 091; DE-A 2 408 168, 2 726 283, 2 639 930, 2 901 520, 3 308 766, 3 320 483, 3 323 699; DD-A 216 476, 214 468, 214 469, EP-A 84 290, 110 214, 115 305, 124 915, 124 877, 144 288, 147 747, 178 165, 161 577; JP-A 75/33 733, 75/21 249, 77/128 130, 77/146 234, 79/0 036, 79/133 131, 81/83 742, 81/87 040, 81/109 345, 83/134 628, 82/22 237, 82/112 749, 83/17 431, 83/21 249, 84/75 249, 84/149 348, 84/182 785, 84/180 557, 84/189 342, 84/228 249, 84/101 650, 79/24 019, 79/25 823, 86/48 856, 86/48 857, 86/27 539, 86/6652, 86/72 040, 87/11 455, 87/62 157, and in Research Disclosure 79/17 901, 79/17 905, 79/18 813, 83/22 827 and 84/24 014.

The photographic layers may also contain further derivatives of hydroquinone ethers. These compounds act as light stabilizers and are particularly suitable for stabilizing magenta dyes. Such compounds and combinations thereof with other additives are described in greater detail, for example, in the publications below: U.S. Pat. Nos. 3,285,937, 3,432 300, 3,519,429, 3,476,772, 3,591,381, 3,573,052, 3,574,627, 3,573,050, 3,698,909, 3,764,337, 3,930,866, 4,113,488, 4,015,990, 4,113,495, 4,120,723, 4,155,765, 4,159,910, 4,178,184, 4,138,259, 4,174,220, 4,148,656, 4,207,111, 4,254,216, 4,134,011, 4,273,864, 4,264,720, 4,279,990, 4,332,886, 4,436,165, 4,360,589, 4,416,978, 4,385,111, 4,459,015, 4,559,297, 4,631,252, 4,616,082; GB-A 1 347 556, 1 366 441, 1 547 392, 1 557 237, 2 135 788; DE-A 3 214 567, 4 008 785, 4 012 305; DD-214 469, EP-A 161 577,167 762, 164 130, 176 845; JP-A 76/123 642, 77/35 633, 77/147 433, 78/126, 78/10 430, 78/53 321, 79/24 019, 79/25 823, 79/48 537, 79/44 521, 79/56 833, 79/70 036, 79/70 830, 79/73 032, 79/95 233, 79/145 530, 80/21 004, 80/50 244, 80/52 057, 80/70 840, 80/139 383, 81/30 125, 81/151 936, 82/34 552, 82/68 833, 82/204 306, 82/204 037, 83/134 634, 83/207 039, 84/60 434, 84/101 650, 84/87 450, 84/149 348, 84/182 785, 86/72 040, 87/11 455, 87/62 157, 87/63 149, 86/2151, 86/6652, 86/48 855, 89/309 058 and in Research Disclosure 78/17 051.

Preferred costabilizers are those of the formulae P, SA, SB, HQ and RE below.

Compounds of the formula P

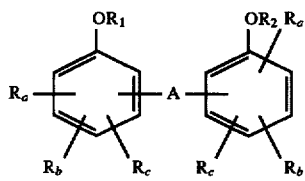

in which

R$_1$ and R$_2$, independently of one another, are hydrogen, acyl or alkyl;

R$_a$, R$_b$ and R$_c$, independently of one another, are H, alkyl, cycloalkyl, aryl, halogen, alkoxy, aroxy, acyloxy, alkylthio, arylthio, acyl, sulfonyl, sulfamoyl, acylamino, sulfonylamino or nitro;

A is a bond, S$\!=\!$O]$_m$, alkylene or —NR$_d$—;

R$_d$ is alkyl or acyl; and m is 0, 1 or 2.

Examples of compounds of the formula P are:

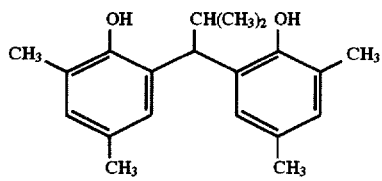

P 1

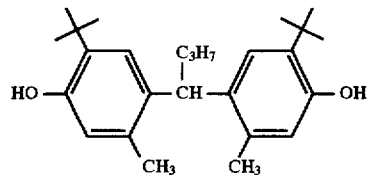

P 2

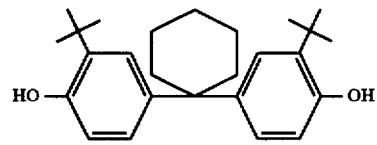

P 3

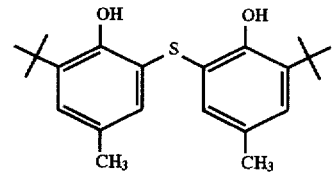

P 4

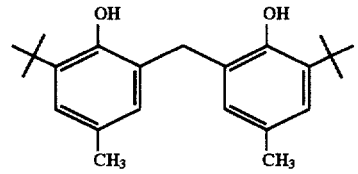

P 5

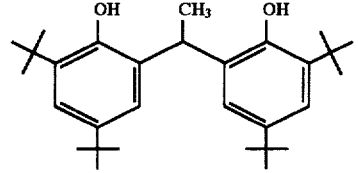

P 6

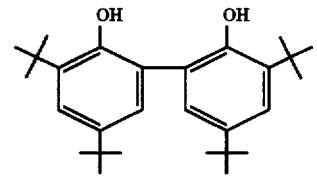

P 7

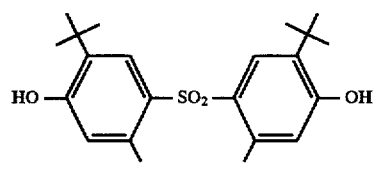

P 8

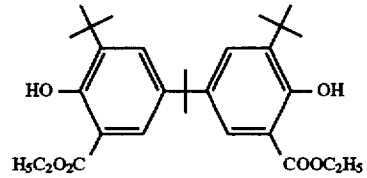

P 9

-continued
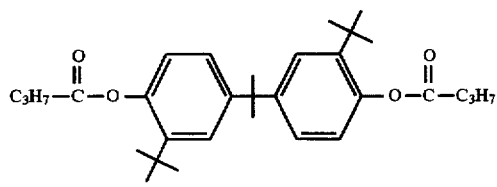
P 10
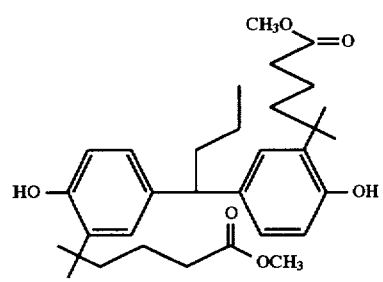
P 11
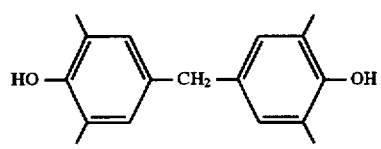
P 12
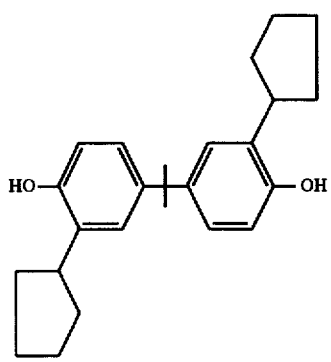
P 13
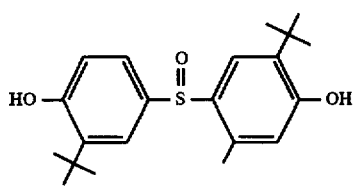
P 14
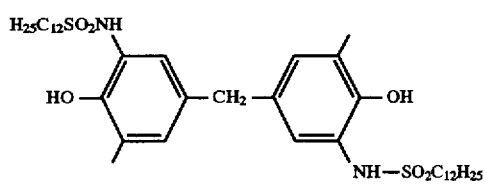
P 15
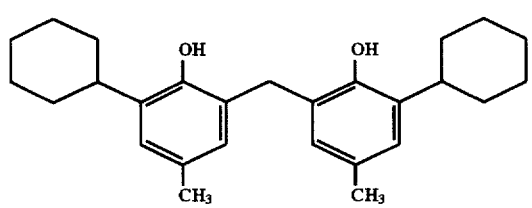
P 16
-continued
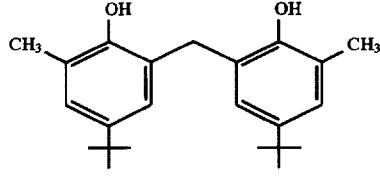
P 17
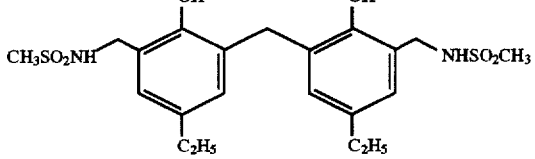
P 18
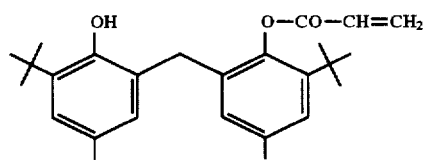
P 19
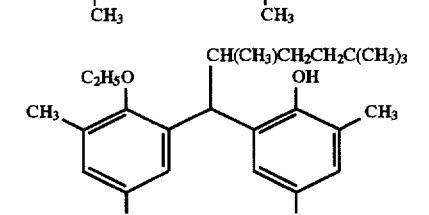
P 20
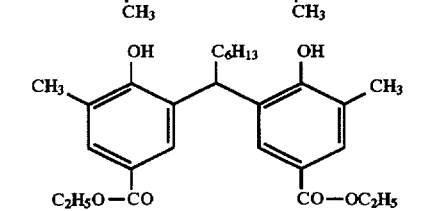
P 21
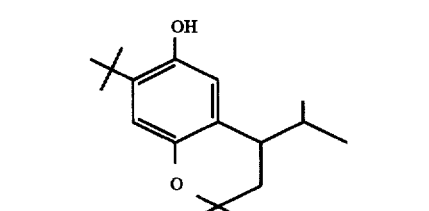
P 22
Compounds of the formula SA
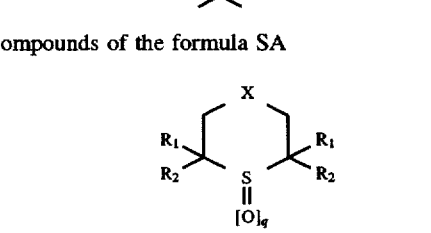
in which
$R_1$ is hydrogen;
$R_2$ is phenyl or
$R_1$ and $R_2$ are methyl;
q is 0, 1 or 2; and
X is a divalent radical which supplements the ring of the formula SA to form a tetrahydrothiopyran ring.
Examples of compounds of the formula SA are those given in U.S. Pat. No. 4,993,271 and

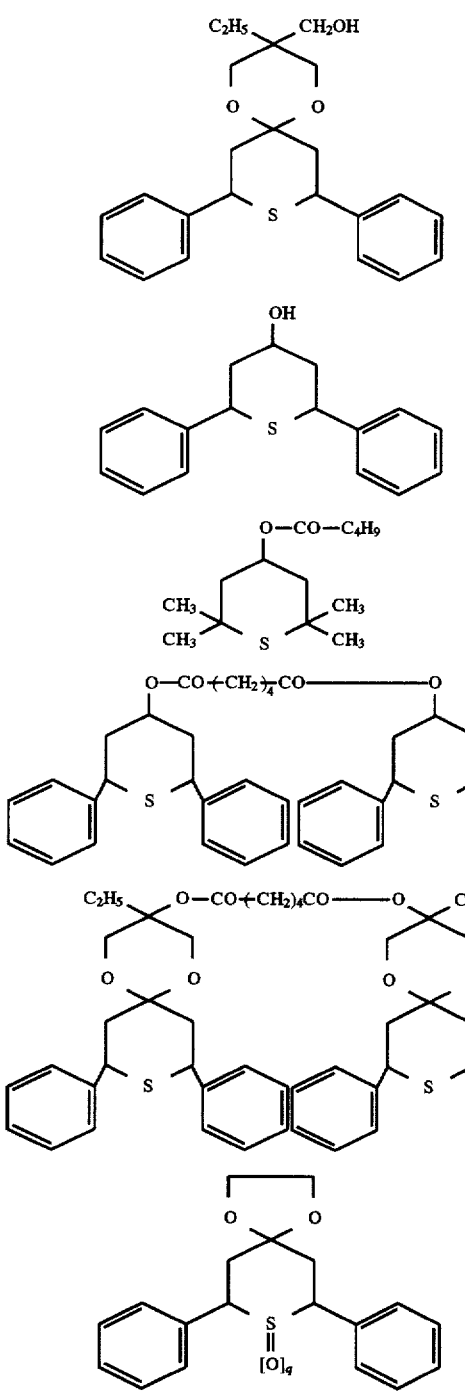

SA 1

SA 2

SA 3

SA 4

SA 5

SA 6

Compounds of the formula SB

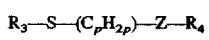

in which

R₃ is alkyl, aryl or a (C$_p$H$_{2p}$)—Z—R₄ group;
p is 1-12;
Z is —CO—O— or —O—CO—; and
R₄ is a univalent, divalent, trivalent or tetravalent group.
Examples of compounds of the formula SB are:

 SB 1

-continued

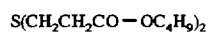 SB 2

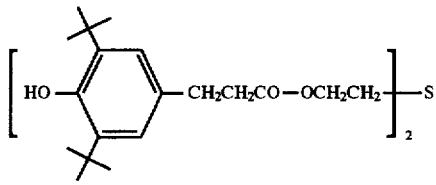 SB 3

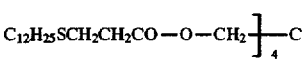 SB 4

Compounds of the formula HQ

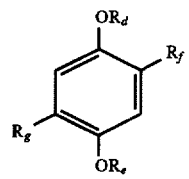

in which

R$_e$ and R$_d$, independently of one another, are alkyl or cycloalkyl; and

R$_f$ and R$_g$, independently of one another, are as defined for R$_a$, R$_b$ and R$_c$.

Examples of compounds of the formula HQ are:

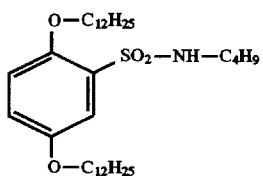 HQ 1

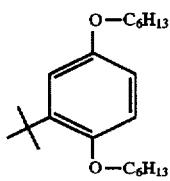 HQ 2

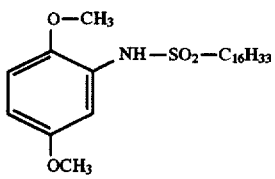 HQ 3

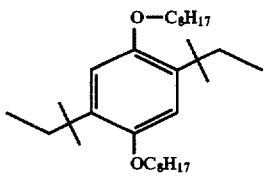 HQ 4

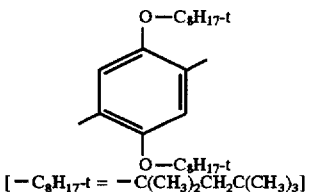 HQ 5

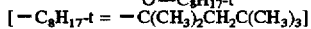

-continued

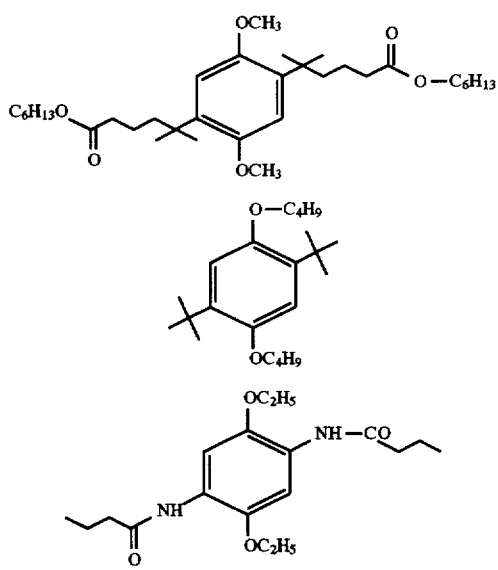

HQ 6

HQ 7

HQ 8

Compounds of the formula RE

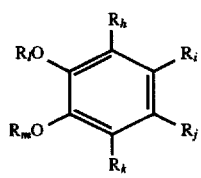

in which

R$_l$ and R$_m$, independently of one another, are H, acyl or alkyl; or R$_l$ and R$_m$ are bonded together to a P—O-aryl radical; and R$_h$, R$_i$, R$_j$ and R$_k$, independently of one another, are as defined for R$_a$, R$_b$ and R$_c$, with the proviso that at least one of the radicals R$_i$ and R$_j$ is not alkyl.

Examples of compounds of the formula RE are:

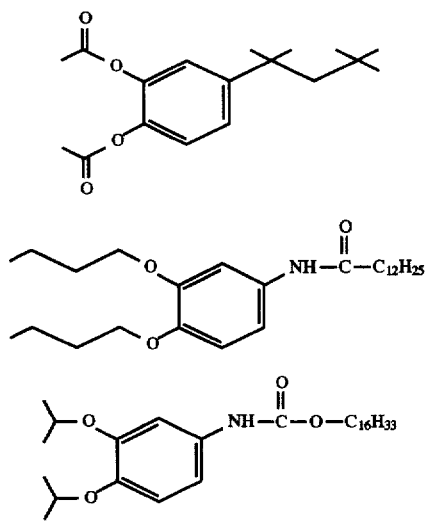

RE 1

RE 2

RE 3

-continued

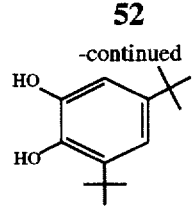

RE 4

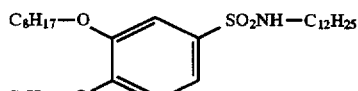

RE 5

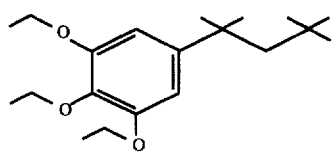

RE 6

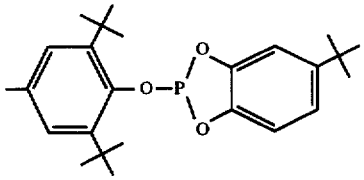

RE 7

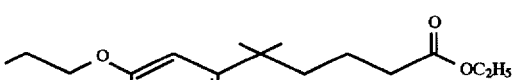

RE 8

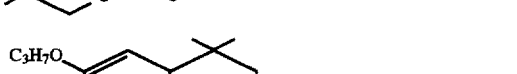

RE 9

Silver-halide emulsions which can be used are conventional silver-chloride, silver-bromide or silver-iodide emulsions or mixtures thereof, such as silver-chlorobromide and silver-chloroiodide emulsions, in which the silver halides may have any known crystal form. The use of silver-chloride emulsions is particularly important in the material according to the invention. The preparation of such emulsions and the sensitization thereof are described in RESEARCH DISCLOSURE, November 1989, No. 307 105. This publication furthermore mentions a number of binders for said emulsions which can also be used in the materials according to the invention. The same applies to the bases mentioned in the publication.

The silver-halide emulsion which can be used for carrying out this invention can be sensitized for all desired wavelengths with the aid of sensitization pigments. For this purpose, it is possible to use cyanine pigments, merocyanine pigments, holopolar pigments, hemicyanine pigments, styryl pigments or hemioxanol pigments.

The photographic layers may furthermore contain conventional plasticizers, such as glycerol. The emulsions may also be cured by means of curing agents which are customary for gelatin. Finally, the emulsions may also contain customary coating auxiliaries.

The present invention thus furthermore relates to colour-photographic recording materials according to claim 1, which contain further organic stabilizers, UV absorbers, optical brighteners, light stabilizers, colour cast inhibitors and/or plasticizers.

The present invention also relates to compounds of the formula

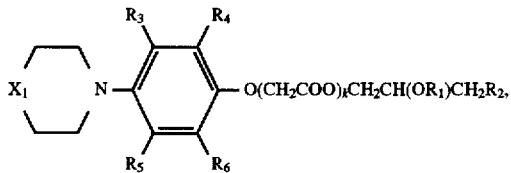
(Ia)

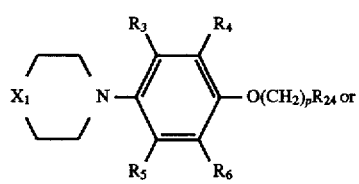
(Ib)

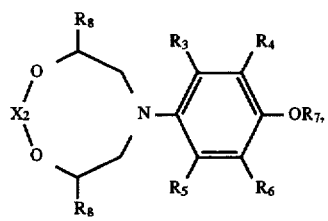
(II)

where
k is the number 0 or 1;
p is a number from 1 to 18;
$R_1$ is hydrogen, $C_1$–$C_{12}$alkyl, $C_1$–$C_{12}$alkoxy, —$COR_9$, —$COOR_{10}$ or —$Si(R_{11})(R_{12})(R_{13})$;
in which $R_9$ is $C_1$–$C_8$alkyl, $C_2$–$C_{18}$alkenyl or phenyl;
$R_{10}$ is $C_1$–$C_4$alkyl or benzyl; and
$R_{11}$, $R_{12}$ and $R_{13}$, independently of one another, are $C_1$–$C_6$alkyl or phenyl;
$R_2$ is hydrogen, $C_1$–$C_{18}$alkyl, —$OR_{14}$ or —$(CH_2)_nCOOR_{15}$;
in which n is a number from 0 to 17;
$R_{14}$ is hydrogen, $C_1$–$C_{18}$alkyl, $C_2$–$C_{18}$alkenyl, phenyl-$C_1$–$C_4$alkyl, $C_3$–$C_{24}$alkyl which is interrupted by one or more —O— atoms, $C_2$–$C_{14}$hydroxyalkyl, phenyl, which may be monosubstituted to trisubstituted by $C_1$–$C_4$alkyl, $C_1$–$C_4$alkoxy or halogen, or is tolyl, $C_5$–$C_6$cycloalkyl or —$COR_{16}$;
$R_{15}$ is $C_1$–$C_{18}$alkyl, $C_2$–$C_{18}$alkenyl or phenyl, which may be monosubstituted to trisubstituted by $C_1$–$C_4$alkyl, $C_1$–$C_4$alkoxy or halogen;
in which $R_{16}$ is $C_1$–$C_{18}$alkyl, $C_2$–$C_{18}$alkenyl or phenyl; $R_3$, $R_4$, $R_5$ and $R_6$, independently of one another, are hydrogen, $C_1$–$C_{12}$alkyl, $C_1$–$C_8$alkoxy, $C_5$–$C_7$cycloalkyl, phenyl, phenyl-$C_1$–$C_4$alkyl or halogen;

$R_7$ is hydrogen, $C_1$–$C_{18}$alkyl, $C_2$–$C_{18}$alkenyl, phenyl-$C_1$–$C_4$alkyl, $C_3$–$C_{24}$alkyl, which is interrupted by one or more —O— atoms, phenyl-$C_1$–$C_4$alkyl, phenyl, which may be monosubstituted to trisubstituted by $C_1$–$C_4$alkyl, $C_1$–$C_4$alkoxy or halogen, or is benzyl, a group of the formula

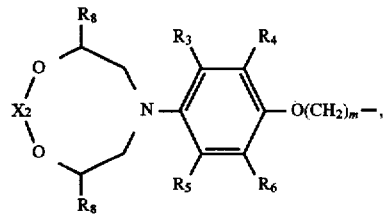

—$CH_2COOR_{23}$ or —$(CH_2COO)_kCH_2CH(OR_1)CH_2R_{17}$;
in which k is the number 0 or 1;
m is a number from 1 to 17;
$R_{17}$ is as defined for $R_2$ or is a group of the formula

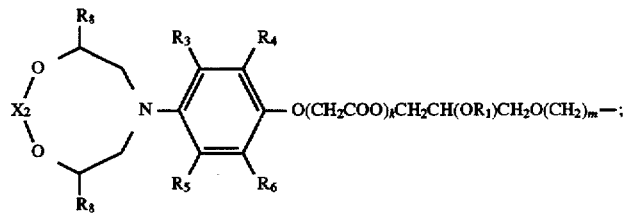

and
$R_{23}$ is $C_1$–$C_8$alkyl;
$R_8$ is hydrogen, $C_1$–$C_{18}$alkyl or $CH_2R_2$;
$R_{24}$ is —$Si(R_{11})(R_{12})(R_{13})$ or a group of the formula

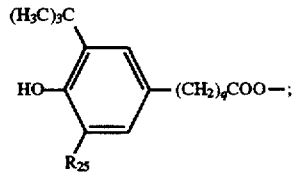

in which q is a number from 0 to 12;
$R_{25}$ is hydrogen or $C_1$–$C_{18}$alkyl;
$X_1$ is O, S, SO, $SO_2$ or $NR_{18}$;
in which $R_{18}$ is hydrogen, $C_1$–$C_{18}$alkyl, —$CH_2CH(OH)CH_2O(C_1$–$C_{14}$alkyl) or
—CO—$R_{19}$;
in which $R_{19}$ is $C_1$–$C_{18}$alkyl; and
$X_2$ is CO, $BR_{20}$, $PR_{21}$, $P(O)R_{22}$, SO or $SO_2$;
in which $R_{20}$, $R_{21}$ and $R_{22}$ are $C_1$–$C_{18}$alkyl or phenyl, which may be monosubstituted to trisubstituted by $C_1$–$C_4$alkyl, $C_1$–$C_4$alkoxy or halogen; and $R_{21}$ and $R_{22}$ may alternatively be phenoxy, which may be monosubstituted to trisubstituted by $C_1$–$C_4$alkyl, $C_1$–$C_4$alkoxy or halogen;

where, in the case of compounds of the formula (Ia) $R_2$ may alternatively be a group of the formula

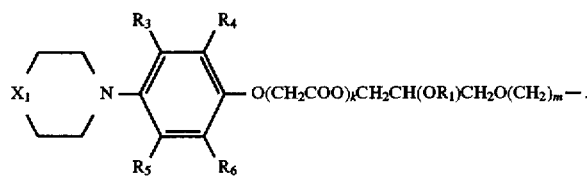

Preference is given to compounds of the formulae (Ia), (Ib) or (II), where k is the number 0 or 1;

p is a number from 2 to 12;

$R_1$ is hydrogen;

$R_2$ is $C_1-C_{18}$alkyl or $-OR_{14}$;
 in which $R_{14}$ is hydrogen, $C_1-C_{18}$alkyl, $C_2-C_{18}$alkenyl, $C_3-C_{24}$alkyl which is interrupted by one or more $-O-$ atoms, phenyl, which may be monosubstituted to trisubstituted by $C_1-C_4$alkyl or $C_1-C_4$alkoxy, or is tolyl or $C_5-C_6$cycloalkyl;

$R_3$, $R_4$, $R_5$ and $R_6$, independently of one another, are hydrogen, $C_1-C_{12}$alkyl or $C_1-C_8$alkoxy;

$R_7$ is $C_1-C_{18}$alkyl, $C_2-C_{18}$alkenyl, a group of the formula

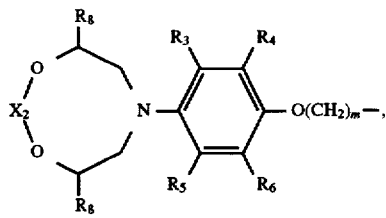

$-CH_2COOR_{23}$ or $-(CH_2COO)_kCH_2CH(OR_1)CH_2R_{17}$;
in which k is the number 0 or 1;
m is a number from 1 to 17;
$R_{17}$ is as defined for $R_2$ or is a group of the formula

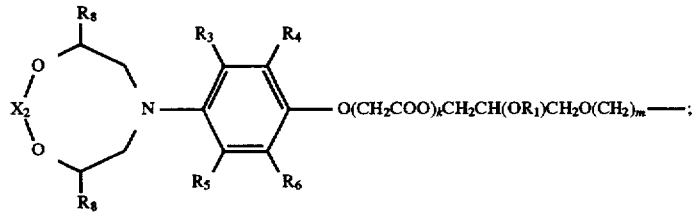

and
$R_{23}$ is $C_1-C_8$alkyl;

$R_8$ is hydrogen, $C_1-C_8$alkyl or $CH_2R_2$;

$R_{24}$ is $-Si(R_{11})(R_{12})(R_{13})$ or a group of the formula

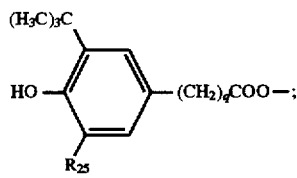

in which q is a number from 0 to 6;

$R_{11}$, $R_{12}$ and $R_{13}$, independently of one another, are $C_1-C_6$alkyl or phenyl; and $R_{25}$ is hydrogen or $C_1-C_{18}$alkyl;

$X_1$ is O, S, $SO_2$ or $NR_{18}$;
in which $R_{18}$ is $-CH_2CH(OH)CH_2O(C_1-C_{14}alkyl)$; and $X_2$ is CO, $BR_{20}$, $PR_{21}$ or $P(O)R_{22}$;
in which $R_{20}$, $R_{21}$ and $R_{22}$ are phenyl, which may be monosubstituted to trisubstituted by $C_1-C_4$alkyl, or $C_1-C_4$alkoxy; and $R_{21}$ and $R_{22}$ may alternatively be phenoxy, which may be monosubstituted to trisubstituted by $C_1-C_4$alkyl or $C_1-C_4$alkoxy;

where, in the case of compounds of the formula (Ia), $R_2$ may alternatively be a group of the formula

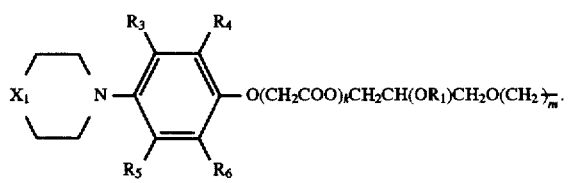

Further preferred compounds are those mentioned in the description of the photographic material.

The novel compounds can be prepared by methods known per se, for example by reacting a compound of the formula

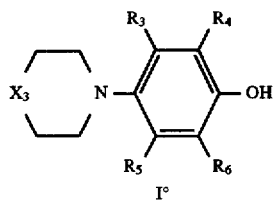

with a glycidyl ether of the formula

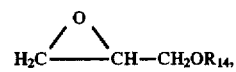

where $X_3$ is O or $SO_2$ and the radicals $R_3$, $R_4$, $R_5$, $R_6$ and $R_{14}$ are as defined in claim 1.

Novel compounds in which $R_1$ is not hydrogen can be prepared by further reaction with an acylating, agent or silylating agent.

Compounds of the formula II can be prepared, for example, by reacting a compound of the formula

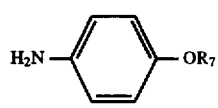

with

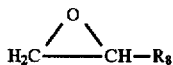

to give

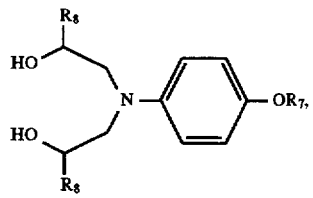

which is then reacted with $R_{22}P(O)Cl_2$, giving

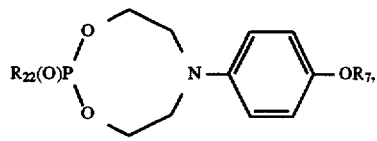

where the substituents are as defined in claim 1.

The dimeric compounds of the formula (Ia) or (II) can be prepared, for example, by reacting a compound of the formula (I°) or the analogous compound (II°) with a bisglycidyl compound of the formula

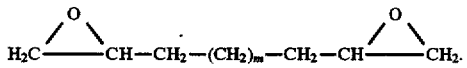

The examples below illustrate the invention in greater detail. In the examples and in the remainder of the description, parts are parts by weight, percentages are percent by weight and

is a tert-butyl radical [an analogous situation also applies to the other alkyl radicals], unless otherwise stated.

EXAMPLE 1

Preparation of 1-morpholino-4-[2'hydroxy-3'-(2"ethylhexyloxy)]propyloxyphenyl

A mixture of 3 g (16.8 mmol) of 4-morpholinophenol, 3.75 g (20 mmol) of 2-ethylhexyl glycidyl ether and 124 mg (0.33 mmol) of ethyltriphenylphosphonium bromide is heated at 130° C. for 4 hours under nitrogen. The crude product is chromatographed over silica gel (ethyl acetate/hexane 6:4), giving 4.7 g (76%) of the compound as a colourless oil (m.p.<30° C.).

Elemental analysis: $C_{21}H_{35}NO_4$ Calculated: C 69.01; H 9.65; N 3.83% Found: C 68.79; H 9.79; N 3.89%

EXAMPLE 2

Preparation of 1-(2-dodecyloxy-tetradecyloxy)-3-(4-morpholin-4-yl-phenoxy)-propan-2-ol (101)

4-Morpholinyl-phenol (12.5 g, 70 mmol), mixture of dodecyl and tetradecyl glycidyl ether (19.7 g, 77 mmol) and ethyltriphenylphosphonium bromide (1.3 g, 3.5 mmol) are reacted as described for compound 100 and the crude product is crystalised from hexane to obtain a white solid 13.4 g (44%) m.p. 49°–52° C.

EXAMPLE 3

Preparation of 1-[4-(1,1-dioxo-thiomorpholin-4-yl)-phenoxy]-3-(2-ethylhexyloxy)-propan-2ol (102)

4-(1,1-dioxo-thiomorpholin-4-yl)phenol (4.1 g, 18 mmol), 2-ethylhexyl glycidyl ether (4.4 g, 23.6 mmol) and ethyltriphenylphosphonium bromide (0.37 g) are heated under nitrogen for 5 h at 145° C. and the crude product is chromatographed over silica gel (hexane/ethylacetate 1:1) to afford a colourless liquid 5.2 g (70%).

Anal. calcd. for $C_{21}H_{35}NO_5S$ C 60.99 H 8.53 N 3.39 C 61.00 H 8.61 N 3.45

EXAMPLE 4

Preparation of 1-[4-(1,1-dioxo-thiomorpholin-4-yl)-phenoxy]-3-(isotridecyloxy)-propan-2-ol (103)

4-(1,1-dioxo-thiomorpholin-4-yl)phenol (2.3 g, 10 mmol), isotridecylglycidyl ether (2.6 g, 10 mmol) and ethyltriphenylphosphonium bromide (0.1 g) are reacted and purified as described for compound 102 to afford a light yellow liquid 2.4 g (50%).

Anal. calcd. for $C_{26}H_{45}NO_5S$ C 64.56 H 9.38 N 2.90 C 64.50 H 9.27 N 2.95

EXAMPLE 5

Preparation of 1-[4-(1,1-dioxo-thiomorpholin-4-yl)-phenoxy]-3-(t-butyloxy)-propan-2-ol (104)

4-(1,1-dioxo-thiomorpholin-4-yl)phenol (2.3 g, 10 mmol), t-butylglycidyl ether (1.56 g, 12 mmol) and ethyltriphenylphosphonium bromide (0.1 g) are reacted and purified as described for compound 102 to afford a light yellow liquid 2.8 g (78%).

EXAMPLE 6

Preparation of 1-[4-(1,1-dioxo-thiomorpholin-4-yl)-phenoxy]-3-(isooctyloxy)-propan-2-ol (105)

4-(1,1-dioxo-thiomorpholin-4-yl)phenol (2.3 g, 10 mmol), isooctylglycidyl ether (1.9 g, 10 mmol) and ethyltriphenylphosphonium bromide (0.2 g) are reacted and purified as described for compound 102 to afford a light yellow liquid 2.85 g (69%).

EXAMPLE 7

Preparation of 1-[4-(1,1-dioxo-thiomorpholin-4-yl)-phenoxy]-3-(3,5,5-trimethylhexyloxy)-propan-2-ol (106)

4-(1,1-dioxo-thiomorpholin-4-yl)phenol (2.3 g, 10 mmol), 3,5,5-trimethylhexylglycidyl ether (2 g, 10 mmol) and ethyltriphenylphosphonium bromide (0.1 g) are reacted and purified as described for compound 102 to afford a light yellow liquid 2.8 g (65%).

EXAMPLE 8

Preparation of 1-[4-(1,1-dioxo-thiomorpholin-4-yl)-phenoxy]-3-(isodecylox)-propan-2-ol (107)

4-(1,1-dioxo-thiomorpholin-4-yl)phenol (2.3 g, 10 mmol), isodecylglycidyl ether (2.15 g, 10 mmol) and ethyltriphenylphosphonium bromide (0.2 g) are reacted and purified as described for compound 102 to afford a light yellow liquid 2.3 g (52%).

Anal. calcd. for $C_{23}H_{39}NO_5S$ C 62.55 H 8.90 N 3.17 C 62.58 H 8.86 N 3.24

EXAMPLE 9

Preparation of 1-[4-(1,1-dioxo-thiomorpholin-4-yl)-phenoxy]-3-(isododecyloxy)-propan-2-ol (108)

4-(1,1-dioxo-thiomorpholin-4-yl)phenol (2.3 g, 10 mmol), isodecylglycidyl ether (2.4 g, 10 mmol) and ethyltriphenylphosphonium bromide (0.2 g) are reacted and purified as described for compound 102 to afford a light yellow liquid 1.4 g (30%).

Anal. calcd. for $C_{25}H_{43}NO_5S$ C 63.93 H 9.23 N 2.98 C 63.97 H 9.06 N 2.99

EXAMPLE 10

Preparation of 1-[4-(1,1-dioxo-thiomorpholin-4-yl)-phenoxy]-3-(dodecyloxy-tetradecyloxy)-propan-2-ol (109)

4-(1,1-dioxo-thiomorpholin-4-yl)phenol (2.3 g, 10 mmol), a mixture of dodecyl/tridecyl/tetradecylglycidyl ether (2.6 g, 10 mmol) and ethyltriphenylphosphonium bromide (0.1 g) are reacted and purified as described for compound 102 to afford a light yellow liquid 2.14 g (45%).

EXAMPLE 11

Preparation of 1-[4-(1,1-dioxo-thiomorpholin-4-yl)-phenoxy]-3-(phenoxy)-propan-2-ol (110)

4-(1,1-dioxo-thiomorpholin-4-yl)phenol (2.3 g, 10 mmol), phenylglycidyl ether (1.5 g, 10 mmol) and ethyltriphenylphosphonium bromide (0.1 g) are reacted and purified as described for compound 102 to afford a light yellow liquid 2.2 g (58%).

EXAMPLE 12

Preparation of 1-[4-(1,1-dioxo-thiomorpholin-4-yl)-phenoxy]-3-(2,2-dimethylhexanol)-propan-2-ol (111)

4-(1,1-dioxo-thiomorpholin-4-yl)phenol (2.3 g, 10 mmol), 2,2-dimethyl-hexanoylglycidyl ether (2.3 g, 10 mmol) and ethyltriphenylphosphonium bromide (0.2 g) are reacted and purified (dioxane/hexane 1:1, eluent) as described for compound 102 to afford a light yellow liquid 3.6 g (79%).

EXAMPLE 13

Preparation of 1-[4-(1,1-dioxo-thiomorpholin-4-yl)-phenoxy]-3-(nonyl)-propan-2-ol (112)

4-(1,1-dioxo-thiomorpholin-4-yl)phenol (2.3 g, 10 mmol), 2-(decyl)-oxirane (1.9 g, 10 mmol) and ethyltriphenylphosphonium bromide (0.2 g) are reacted and purified as described for compound 102 to afford a light brown solid 1.6 g (38%), m.p. 84° C.

EXAMPLE 14

Preparation of 1-[4-(1,1-dioxo-thiomorpholin-4-yl)-phenoxy]-3-(2,2,4-trimethyl-3-hydroxy-pentyloxy)-propan-2-ol (114)

4-(1,1-dioxo-thiomorpholin-4-yl)phenol (1.13 g, 5 mmol), 2,2,4-trimethyl-3-hydroxy-pentyloxyglycidyl ether (1.0 g, 5 mmol) and ethyltriphenylphosphonium bromide (0.1 g) are reacted and purified as described for compound 102 to afford a light yellow liquid 0.86 g (40%).

EXAMPLE 15

Preparation of 1-[3-(3,5-di t-butyl-4-hydroxy-phenyl)-propane-carboxy)-2-(4-morpholin-4-yl phenoxy)-ethane (118)

2-(4-Morpholinyl-phenoxy)-ethanol (1.12 g, 5 mmol), methyl 3,5-di t-butyl-4-hydroxyphenyl propionic acid (1.38 g, 5 mmol) and dibutyltinoxide (0.12 g, 0.5 mmol in xylene (30 ml)) are heated at 140° C. under nitrogen for 5 h and the crude product is chromatographed over silicagel (ethyl acetate/hexane, 3:7) to obtain a white solid 0.5 g (21%) m.p. 105°–109° C.

EXAMPLE 16

Preparation of 1-[3-(3-t-butyl-5-methyl-4-hydroxy-phenyl)-propane-carboxy)-2-(4-morpholin-4-yl phenoxy)-ethane (119)

2-(4-Morpholinyl-phenoxy)-ethanol (1.12 g, 5 mmol), methyl 3-t-butyl-5-methyl-4-hydroxyphenyl propionic acid (1.25 g, 5 mmol) and dibutyltinoxide (0.12 g, 0.5 mmol in xylene (30 ml)) are heated at 140° C. under nitrogen and the product is purified as described for compound 118 to obtain a light yellow oil 1.72 g (78%).

EXAMPLE 17

Preparation of 4,8-bis-butoxymethyl-6-(4-dodecyloxy-phenyl)-2-phenyl-[1,3,6,2] dioxazaphosphocane-2-oxide (200)

To a solution of 4-dodecyloxy-N,N-di(2-hydroxy-3-butoxy)-propyl aniline (5.38 g, 10 mmol), pyridine (3 g, 30 mmol) and dimethylaminopyridine (0.2 g) in dichloromethane (20 ml) is added a solution of phenylphosphonous dichloride (2.14 g, 11 mmol) in dichloromethane (5 ml) at 0° C. and then stirred at room temperature for 6 h. After treating with water, the crude product is purified over silicagel (ethyl acetate/hexane, 1:1) to afford a light yellow solid 1.2 g (18%, compound 200) and a white solid 1.3 g (20%, another isomer).

EXAMPLE 18

Preparation of 4,8-bis-butoxymethyl-6-(4-dodecyloxy-phenyl)-2-phenoxy-[1,3,6,2] dioxazaphosphocane-2-oxide (201)

It is prepared from 4-dodecyloxy-N,N-di(2-hydroxy-3-butoxy)-propyl aniline (5.38 g, 10 mmol), pyridine (3 g, 30 mmol), dimethylaminopyridine (0.2 g) and phenylphosphonic dichloride (2.32 g, 11 mmol) in dichloromethane as described for compound 200 to obtain a white solid 1.44 g (21%) and its isomer 1.4 g (20% a white solid).

EXAMPLE 19

Preparation of 6-(4-dodecyloxy-phenyl)-2-phenyl-[1,3,6,2]dioxazaphosphocane-2-oxide (202)

It is prepared from 4-dodecyloxy-N,N-di(2-hydroxy)ethyl aniline (3.66 g, 10 mmol), pyridine (2 g, 25 mmol), dimethylaminopyridine (0.2 g) and phenylphosphonous dichloride (2.15 g, 11 mmol) in dichloromethane as described for compound 200 to obtain a white solid 1 g (21%).

EXAMPLE 20

Preparation of 6-(4-dodecyloxy-phenyl)-2-phenoxy-[1,3,6,2]dioxazaphosphocane-2-oxide (203)

It is prepared from 4-dodecyloxy-N,N-di(2-hydroxy)-ethyl aniline (3.66 g, 10 mmol), pyridine (2 g, 25 mmol), dimethylaminopyridine (0.2 g) and phenylphosphonic dichloride (2.11 g, 10 mmol) in dichloromethane as described for compound 200 to obtain a white solid 1.3 g (25%).

EXAMPLE 21

Preparation of 6-(4-methoxy-phenyl)-2-phenoxy-[1,3,6,2]dioxazaphosphocane-2-oxide (204)

It is prepared from 4-methoxy-N,N-di(2-hydroxy)-ethyl aniline (2.1 g, 10 mmol), pyridine (2 g, 25 mmol), dimethylaminopyridine (0.2 g) and phenylphosphonic dichloride (2.11 g, 10 mmol) in dichloromethane as described for compound 200 to obtain a white solid 1.2 g (34%); m.p. 124°–126° C.

EXAMPLE 22

Preparation of 4,8-bis-butoxymethyl-6-(4-methoxy-phenyl)-2-phenoxy-[1,3,6,2]dioxazaphosphocane-2-oxide (205)

It is prepared from 4-methoxy-N,N-di(2-hydroxy-3-butoxy)-propyl aniline (1.91 g, 5 mmol), pyridine (1,2 g, 15 mmol), dimethylaminopyridine (0.2 g) and phenylphosphonic dichloride (1.1 g, 5.1 mmol) in dichloromethane as described for compound 200 to obtain a pale yellow liquid 0.4 g (16%) and its isomer 0.5 g (19% a pale yellow liquid).

EXAMPLE 23

Preparation of 4,8-bis-butoxymethyl-6-(4-methoxy-phenyl)-2-phenyl-[1,3,6,2]dioxazaphosphocane-2-oxide (206)

It is prepared from 4-methoxy-N,N-di(2-hydroxy-3-butoxy)-propyl aniline (1.91 g, 5 mmol), pyridine (1,2 g, 15 mmol), dimethylaminopyridine (0.2 g) and phenylphosphonous dichloride (1 g, 5.1 mmol) in dichloromethane as described for compound 200 to obtain a colourless liquid 0.6 g (24%) and its isomer 0.6 g (24% a colourless liquid).

EXAMPLE 24

Preparation of 4,8-bis-(2-ethyl-hexyloxymethyl)-6-(4-dodecyloxy-phenyl)-2-phenyl-[1,3,6,2]dioxazaphosphocane-2-oxide (207)

It is prepared from 4-methoxy-N,N-di(2-hydroxy-3-ethyl-hexyloxy)-propyl aniline (2 g, 4 mmol), pyridine (0,8 g, 10 mmol), dimethylaminopyridine (0.2 g) and phenylphosphonous dichloride (0.8 g, 4 mmol) in dichloromethane as described for compound 200 to obtain a pale yellow liquid 0.8 g (32%) and its isomer 0.85 g (34%, a pale yellow liquid).

EXAMPLE 25

Preparation of 6-(4-dodecyloxy-phenyl)-[1,3,6,2]dioxthiazocane-2-oxide (208)

It is prepared from 4-dodecyloxy-N,N-di(2-hydroxy)-ethyl aniline (1.8 g, 5 mmol), pyridine (0,95 g, 6 mmol), dimethylaminopyridine (0.2 g) and thionyl chloride (0.72 g, 6 mmol) in dichloromethane as described for compound 200 to obtain a white solid 1.1 g (53%).

Anal. calcd. for $C_{22}H_{37}NO_4S$ C 64.20 H 9.06 N 3.40 S 7.79 C 63.99 H 9.07 N 3.30 S 7.85

EXAMPLE 26

A polyethylene-coated base material is coated with a gelatin layer containing silver bromide, magenta coupler (M-11) and a stabilizer.

The gelatin layer contains the following components (per $m^2$ of base material):

TABLE 1

| Component | AgBr layer |
|---|---|
| Gelatin | 5.10 g |
| Curing agent | 300 mg |
| Wetting agent | 85 mg |
| Silver bromide | 260 mg |
| Magenta coupler | 305 mg |
| Tricresyl phosphate | 305 mg |
| Stabilizer | 229 mg |

The stabilizer is used either alone or as a mixture with a costabilizer, in which case the stabilizer:costabilizer ratio is 4.5:3.5; the total amount of stabilizer remains constant.

The curing agent used is 2,4-dichloro-6-hydroxytriazine, and the wetting agent used is the sodium salt of diisobutyl-naphthalenesulfonic acid.

A step wedge having a density difference of 0.15 logE per step is exposed onto each of the resultant samples, which are subsequently processed in accordance with the manufacturer's instructions by the Kodak EP2 process for colour negative papers.

After exposure and processing, the remission density in green for the magenta step is measured at a density between 0.9 and 1.1 of the wedge. The wedge is then exposed behind a UV absorber filter in an Atlas exposure unit with 15 $kJ/cm^2$, and the remission density is re-measured. The drop in magenta dye density (–ΔD) is greatly reduced in the presence of the stabilizers compared with a sample containing no stabilizer (Table 1a to 1c).

TABLE 1a

| | % dye loss | | |
|---|---|---|---|
| | | with costabilizer | |
| stabilizer | alone | P1 | P2 |
| no | 50 | | |
| 100 | 13 | 7 | 10 |
| 101 | 12 | 8 | 10 |
| 102 | 13 | 8 | 11 |
| 103 | 12 | 7 | 10 |
| 104 | 33 | 13 | 18 |
| 105 | 15 | 8 | 12 |
| 106 | 13 | 8 | 11 |
| 107 | 11 | 6 | 10 |
| 108 | 12 | 6 | 9 |
| 109 | 13 | 8 | 10 |
| 111 | 10 | 7 | 11 |
| 112 | 16 | 7 | 11 |
| 114 | 44 | 11 | 21 |
| 118 | 15 | 9 | 13 |
| 119 | 11 | 7 | 10 |

TABLE 1b

| stabilizer | % dye loss alone | with costabilizer P1 | P2 |
|---|---|---|---|
| no stabilizer | 55 | | |
| 200 | 20 | 10 | 15 |
| 201 | 22 | 11 | 17 |
| 202 | 23 | 11 | 16 |
| 203 | 22 | 12 | 15 |
| 204 | 21 | 9 | 16 |
| 205 | 21 | 9 | 14 |
| 206 | 20 | 9 | 16 |
| 207 | 21 | 12 | 14 |
| 208 | 27 | 15 | 19 |

TABLE 1c

| stabilizer | % dye loss alone | with costabilizer SA1 | SB3 | HQ6 | RE9 |
|---|---|---|---|---|---|
| no stabilizer | 57 | | | | |
| 100 | 13 | 9 | 11 | 13 | 12 |
| 102 | 9 | 8 | 12 | 13 | 10 |
| 203 | 19 | 17 | 19 | 18 | 19 |

EXAMPLE 27

A polyethylene-coated base material is coated with a gelatin layer containing silver bromide, magenta coupler (M-5) and a stabilizer.

The gelatin layer contains the following components (per m² of base material):

TABLE 2

| Component | AgBr layer |
|---|---|
| Gelatin | 5.10 g |
| Curing agent | 300 mg |
| Wetting agent | 85 mg |
| Silver bromide | 260 mg |
| Magenta coupler | 306 mg |
| Tricresyl phosphate | 612 mg |
| Stabilizer | 107 mg |

The stabilizer is used either alone or as a mixture with a costabilizer, in which case the stabilizer:costabilizer ratio is 1:1; the total amount of stabilizer remains constant.

The curing agent used is 2,4-dichloro-6-hydroxytriazine, and the wetting agent used is the sodium salt of diisobutylnaphthalenesulfonic acid.

A step wedge having a density difference of 0.15 logE per step is exposed onto each of the resultant samples, which are subsequently processed in accordance with the manufacturer's instructions by the Kodak EP2 process for colour negative papers.

After exposure and processing, the remission density in green for the magenta step is measured at a density between 0.9 and 1.1 of the wedge. The wedge is then exposed behind a UV absorber filter in an Atlas exposure unit with 30 kJ/cm², and the remission density is re-measured. The drop in magenta dye density (−ΔD) is greatly reduced in the presence of the stabilizers compared with a sample containing no stabilizer Table 2a and 2b).

TABLE 2a

| stabilizer | % dye loss alone | with costabilizer P1 | P2 |
|---|---|---|---|
| no | 45 | | |
| 100 | 12 | 12 | 20 |
| 101 | 11 | 12 | 19 |
| 102 | 10 | 14 | 23 |
| 103 | 10 | 11 | 22 |
| 104 | 28 | 29 | 34 |
| 105 | 12 | 14 | 22 |
| 106 | 10 | 13 | 23 |
| 107 | 10 | 11 | 22 |
| 108 | 10 | 13 | 22 |
| 109 | 10 | 13 | 23 |
| 110 | 35 | 32 | 38 |
| 111 | 10 | 12 | 26 |
| 112 | 9 | 9 | 21 |
| 114 | 41 | 32 | 38 |
| 118 | 18 | 17 | 25 |
| 119 | 12 | 16 | 22 |

TABLE 2b

| stabilizer | % dye loss alone | with costabilizer P1 | P2 |
|---|---|---|---|
| no | 45 | | |
| 200 | 21 | 17 | 28 |
| 201 | 23 | 16 | 29 |
| 202 | 21 | 13 | 23 |
| 203 | 22 | 14 | 27 |
| 204 | 19 | 17 | 29 |
| 205 | 21 | 13 | 26 |
| 206 | 23 | 12 | 28 |
| 207 | 18 | 15 | 27 |
| 208 | 33 | 15 | 26 |

What is claimed is:

1. A colour-photographic recording material which comprises a magenta coupler and, as stabilizer, at least one compound of the formula

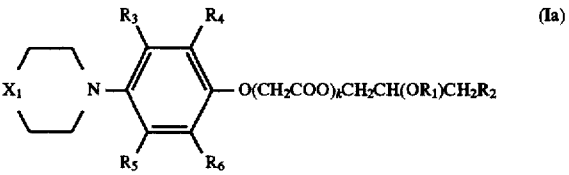

(Ia)

where k is the number 0 or 1;

$R_1$ is hydrogen, $C_1$–$C_{12}$alkyl, $C_1$–$C_{12}$alkoxy, —$COR_9$, —$COOR_{10}$ or —$Si(R_{11})(R_{12})(R_{13})$;

in which $R_9$ is $C_1$–$C_8$alkyl, $C_2$–$C_{18}$alkenyl or phenyl;

$R_{10}$ is $C_1$–$C_4$alkyl or benzyl; and $R_{11}$, $R_{12}$ and $R_{13}$, independently of one another, are $C_1$–$C_6$alkyl or phenyl;

$R_2$ is hydrogen, $C_1$–$C_{18}$alkyl, —$OR_{14}$ or —$(CH_2)_n COOR_{15}$;

in which n is a number from 0 to 17;

$R_{14}$ is hydrogen, $C_1$–$C_{18}$alkyl, $C_2$–$C_{18}$alkenyl, phenyl-$C_1$–$C_4$alkyl, $C_3$–$C_{24}$alkyl which is interrupted by one or more —O— atoms, $C_2$–$C_{14}$hydroxyalkyl, phenyl, which may be monosubstituted to trisubstituted by $C_1$–$C_4$alkyl, $C_1$–$C_4$alkoxy or halogen, or is tolyl, $C_5$–$C_6$cycloalkyl or —$COR_{16}$;

$R_{15}$ is $C_1$–$C_{18}$alkyl, $C_2$–$C_{18}$alkenyl or phenyl, which may be monosubstituted to trisubstituted by $C_1$–$C_4$alkyl, $C_1$–$C_4$alkoxy or halogen;

in which $R_{16}$ is $C_1$–$C_{18}$alkyl, $C_2$–$C_{18}$alkenyl or phenyl;

$R_3$, $R_4$, $R_5$ and $R_6$, independently of one another, are hydrogen, $C_1$–$C_{12}$alkyl, $C_1$–$C_8$alkoxy, $C_5$–$C_7$cycloalkyl, phenyl, phenyl-$C_1$–$C_4$alkyl or halogen;

$X_1$ is O, S, SO, $SO_2$ or $NR_{18}$;

in which $R_{18}$ is hydrogen, $C_1$–$C_{18}$alkyl, —$CH_2CH(OH)CH_2O(C_1$–$C_{14}$alkyl) or —CO—$R_{19}$;

in which $R_{19}$ is $C_1$–$C_{18}$alkyl; and where, in the case of compounds of the formula (Ia) $R_2$ may alternatively be a group of the formula

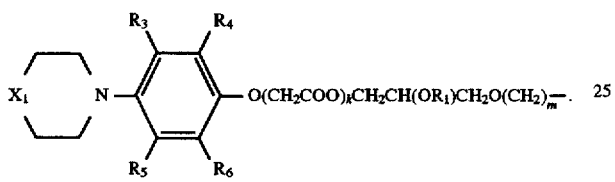

2. A color-photographic recording material according to claim 1, which comprises, as stabilizer, at least one compound of the formula (Ia)

where k is the number 0 or 1;

$R_1$ is hydrogen;

$R_2$ is $C_1$–$C_{18}$alkyl or —$OR_{14}$;

in which $R_{14}$ is hydrogen, $C_1$–$C_{18}$alkyl, $C_2$–$C_{18}$alkenyl, $C_3$–$C_{24}$alkyl which is interrupted by one or more —O— atoms, phenyl, which may be monosubstituted to trisubstituted by $C_1$–$C_4$alkyl or $C_1$–$C_4$alkoxy, or is tolyl or $C_5$–$C_6$cycloalkyl;

$R_3$, $R_4$, $R_5$ and $R_6$, independently of one another, are hydrogen, $C_1$–$C_{12}$alkyl or $C_1$–$C_8$alkoxy;

$X_1$ is O, S, SO, $SO_2$ or $NR_{18}$;

in which $R_{18}$ is —$CH_2CH(OH)CH_2O(C_1$–$C_{14}$alkyl); and where, in the case of compounds of the formula (Ia), $R_2$ may alternatively be a group of the formula

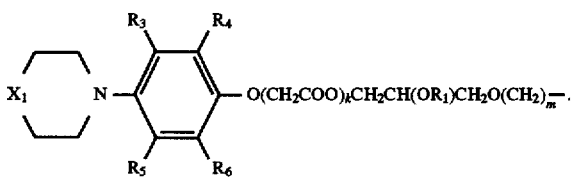

3. A color-photographic recording material according to claim 1, which contains further organic stabilizers, UV absorbers, optical brighteners, light stabilizers, colour cast inhibitors and/or plasticizers.

4. A color-photographic recording material according to claim 3, which comprises, as further organic stabilizers, a compound of the formula P

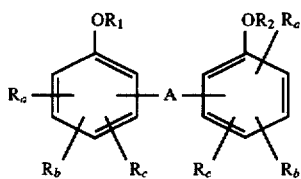

in which $R_1$ and $R_2$, independently of one another, are hydrogen, acyl or alkyl;

$R_a$, $R_b$ and $R_c$, independently of one another, are H, alkyl, cycloalkyl, aryl, halogen, alkoxy, aroxy, acyloxy, alkylthio, arylthio, acyl, sulfonyl, sulfamoyl, acylamino, sulfonylamino or nitro;

A is a bond, $S\!=\!O]_m$, alkylene or $NR_d$;

$R_d$ is alkyl or acyl; and m is 0, 1 or 2;

or a compound of the formula SA

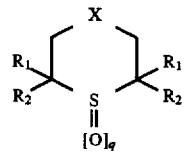

in which $R_1$ is hydrogen;

$R_2$ is phenyl or $R_1$ and $R_2$ are methyl;

q is 0, or 2; and

X is a divalent radical which supplements the ring of the formula SA to form a tetrahydrothiopyran ring;

or a compound of the formula SB

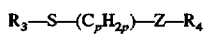

in which $R_3$ is alkyl, aryl or a $(C_pH_{2p})$—Z—$R_4$ group;

p is 1–12;

Z is —CO—O— or —O—CO—; and $R_4$ is a univalent, divalent, trivalent or tetravalent group;

or a compound of the formula HQ

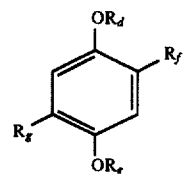

in which $R_e$ and $R_g$, independently of one another, are alkyl or cycloalkyl; and $R_f$ and $R_g$, independently of one another, are as defined for $R_a$, $R_b$ and $R_c$;

or a compound of the formula RE

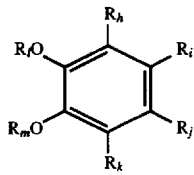

in which

R$_l$ and R$_m$, independently of one another, are H, acyl or alkyl; or R$_l$ and R$_m$ are bonded together to a P—O-aryl radical; and R$_h$, R$_i$, R$_j$ and R$_k$, independently of one another, are as defined for R$_a$, R$_b$ and R$_c$, with the proviso that at least one of the radicals R$_i$ and R$_j$ is not alkyl.

5. A compound of the formula

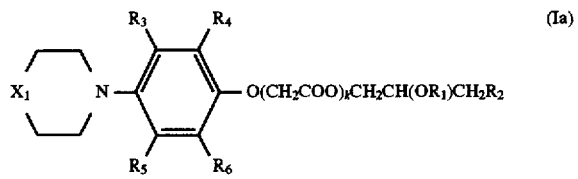

(Ia)

where k is the number 0 or 1;

R$_1$ is hydrogen, C$_1$-C$_{12}$alkyl, C$_1$-C$_{12}$alkoxy, —COR$_9$, —COOR$_{10}$ or —Si(R$_{11}$)(R$_{12}$)(R$_{13}$);
in which R$_9$ is C$_1$-C$_8$alkyl, C$_2$-C$_{18}$alkenyl or phenyl;
R$_{10}$ is C$_1$-C$_4$alkyl or benzyl; and
R$_{11}$, R$_{12}$ and R$_{13}$, independently of one another, are C$_1$-C$_6$alkyl or phenyl;

R$_2$ is hydrogen, C$_1$-C$_{18}$alkyl, —OR$_{14}$ or —(CH$_2$)$_n$COOR$_{15}$;
in which n is a number from 0 to 17;
R$_{14}$ is hydrogen, C$_1$-C$_{18}$alkyl, C$_2$-C$_{18}$alkenyl, phenyl-C$_1$-C$_4$alkyl, C$_3$-C$_{24}$alkyl which is interrupted by one or more —O— atoms, C$_2$-C$_{14}$hydroxyalkyl, phenyl, which may be monosubstituted to trisubstituted by C$_1$-C$_4$alkyl, C$_1$-C$_4$alkoxy or halogen, or is tolyl, C$_5$-C$_6$cycloalkyl or —COR$_{16}$;
R$_{15}$ is C$_1$-C$_{18}$alkyl, C$_2$-C$_{18}$alkenyl or phenyl, which may be monosubstituted to trisubstituted by C$_1$-C$_4$alkyl, C$_1$-C$_4$alkoxy or halogen;
in which R$_{16}$ is C$_1$-C$_{18}$alkyl, C$_2$-C$_{18}$alkenyl or phenyl;

R$_3$, R$_4$, R$_5$ and R$_6$, independently of one another, are hydrogen, C$_1$-C$_{12}$alkyl, C$_1$-C$_8$alkoxy, C$_5$-C$_7$cycloalkyl, phenyl, phenyl-C$_1$-C$_4$alkyl or halogen;

X$_1$ is O, S, SO, SO$_2$ or NR$_{18}$;
in which R$_{18}$ is hydrogen, C$_1$-C$_{18}$alkyl, —CH$_2$CH(OH)CH$_2$O(C$_1$-C$_{14}$alkyl) or —CO—R$_{19}$;
in which R$_{19}$ is C$_1$-C$_{18}$alkyl; and where, in the case of compounds of the formula (Ia) R$_2$ may alternatively be a group of the formula

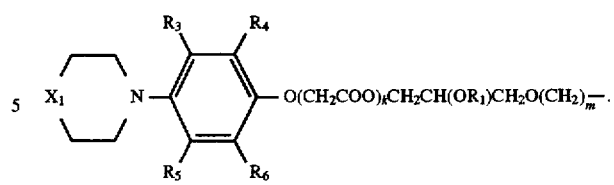

6. A compound according to claim 5,
where
k is the number 0 or 1;
R$_1$ is hydrogen;
R$_2$ is C$_1$-C$_{18}$alkyl or —OR$_{14}$;
in which R$_{14}$ is hydrogen, C$_1$-C$_{18}$alkyl, C$_2$-C$_{18}$alkenyl, C$_3$-C$_{24}$alkyl which is interrupted by one or more —O— atoms, phenyl, which may be monosubstituted to trisubstituted by C$_1$-C$_4$alkyl or C$_1$-C$_4$alkoxy, or is tolyl or C$_5$-C$_6$cycloalkyl;
R$_3$, R$_4$, R$_5$ and R$_6$, independently of one another, are hydrogen, C$_1$-C$_{12}$alkyl or C$_1$-C$_8$alkoxy;
X$_1$ is O, S, SO, SO$_2$ or NR$_{18}$;
in which R$_{18}$ is —CH$_2$CH(OH)CH$_2$O(C$_1$-C$_{14}$alkyl); and
where, in the case of compounds of the formula (Ia), R$_2$ may alternatively be a group of the formula

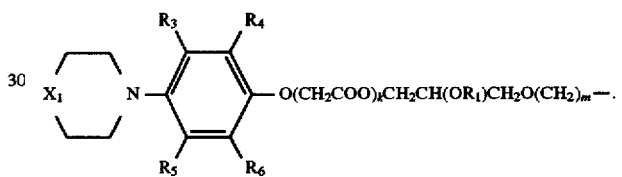

7. A compound according to claim 5,
where
k is the number 0;
R$_1$ is hydrogen;
R$_2$ is —OR$_{14}$;
in which R$_{14}$ is C$_1$-C$_{18}$alkyl, C$_3$-C$_{24}$alkyl which is interrupted by one or more —O— atoms, or phenyl;
R$_3$, R$_4$, R$_5$ and R$_6$ are hydrogen;
X$_1$ is O or SO$_2$.

8. A compound according to claim 5, of the formula

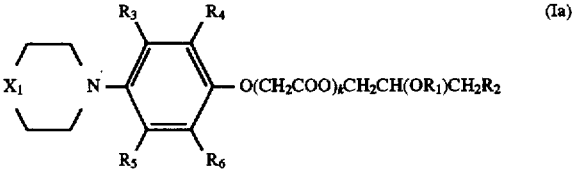

(Ia)

where
k is the number 0;
R$_1$ is hydrogen;
R$_2$ is —OR$_{14}$;
in which R$_{14}$ is C$_1$-C$_{14}$alkyl or phenyl;
R$_3$, R$_4$, R$_5$ and R$_6$ are hydrogen;
X$_1$ is O or SO$_2$; and
X$_1$ is O or SO$_2$.

9. A process for stabilizing magenta couplers and/or magenta dyes in color-photographic materials, in which a stabilizer according to claim 1 is incorporated into the material.

* * * * *